United States Patent
Andre et al.

(10) Patent No.: US 10,329,348 B2
(45) Date of Patent: *Jun. 25, 2019

(54) TREATMENT OF CANCERS USING ANTI-NKG2A AGENTS

(71) Applicant: INNATE PHARMA, Marseilles (FR)

(72) Inventors: Pascale Andre, Marseilles (FR); Mathieu Blery, Marseilles (FR); Caroline Soulas, Marseilles (FR); Nicolai Wagtmann, Cassis (FR)

(73) Assignee: INNATE PHARMA, Marseilles (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,401

(22) PCT Filed: Oct. 23, 2015

(86) PCT No.: PCT/EP2015/074581
§ 371 (c)(1),
(2) Date: Apr. 24, 2017

(87) PCT Pub. No.: WO2016/062851
PCT Pub. Date: Apr. 28, 2016

(65) Prior Publication Data
US 2017/0313773 A1     Nov. 2, 2017

Related U.S. Application Data

(60) Provisional application No. 62/067,642, filed on Oct. 23, 2014.

(51) Int. Cl.
C07K 16/00 (2006.01)
C07K 16/28 (2006.01)
A61K 39/00 (2006.01)

(52) U.S. Cl.
CPC ...... C07K 16/2803 (2013.01); C07K 16/2863 (2013.01); *A61K 2039/505* (2013.01); *A61K 2039/507* (2013.01); *A61K 2039/545* (2013.01); *C07K 2317/24* (2013.01); *C07K 2317/565* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,206,709 B2* | 6/2012 | Spee | C07K 16/2851 424/133.1 |
| 8,796,427 B2 | 8/2014 | Spee et al. | |
| 8,901,283 B2 | 12/2014 | Spee et al. | |
| 8,993,319 B2 | 3/2015 | Moretta et al. | |
| 9,422,368 B2 | 8/2016 | Spee et al. | |
| 2015/0071929 A1 | 3/2015 | Spee et al. | |
| 2015/0125464 A1 | 5/2015 | Moretta et al. | |
| 2015/0132316 A1 | 5/2015 | Moretta et al. | |

FOREIGN PATENT DOCUMENTS

| WO | WO 2006/070286 | 7/2006 |
|---|---|---|
| WO | WO 2008/009545 | 1/2008 |
| WO | WO 2009/092805 | 7/2009 |

OTHER PUBLICATIONS

Katou et al (Cancer Research, 2007, 67(23): 11195-11201).*
Price et al (Current Treatment Options in Oncology, 2012m 13: 35-46).*
Innate Pharma, "IPH 2201—cancer épidermoïde de la tête at du cou" Apr. 10, 2014, retrieved on Dec. 1, 2015 from the internet, URL:http://www.lybsoo.fr/forum/topic/iph-2201-cancer-%C3%A9pidermo%C3%AFde-t%C3%AAte-et-du-cou, pp. 1-75, XP055232711.
Innate Pharma [Online], "R&D Update" Apr. 10, 2014, retrieved on Dec. 1, 2015 from the Internet, URL:http://innate-pharma.com/sites/default/files/14010_rd_day_final_0.pdf, pp. 1-108, XP055232714.
Written Opinion in International Application No. PCT/EP2015/074581, dated Jan. 20, 2016, pp. 1-6.
Duray, A. et al. "Immune Suppression in Head and Neck Cancers: A Review" *Clinical and Developmental Immunology*, 2010, pp. 1-15, vol. 2010, Article ID 701657.

* cited by examiner

*Primary Examiner* — Sean E Aeder
(74) *Attorney, Agent, or Firm* — Saliwanchik, Lloyd & Eisenschenk

(57) ABSTRACT

The present invention relates to HLA-E as a tumor escape mechanism in head and neck cancer. The invention relates to methods for the treatment of head and neck cancer, notably HLA-E expressing head and neck squamous cell carcinoma, using antibodies that specifically bind and inhibit human NKG2A.

15 Claims, 7 Drawing Sheets

Specification includes a Sequence Listing.

SEQUENCE LISTING

<160> NUMBER OF SEQ ID NOS: 17

<210> SEQ ID NO 1
<211> LENGTH: 233
<212> TYPE: PRT
<213> ORGANISM: Homo sapiens

<400> SEQUENCE: 1

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
    210                 215                 220

Ile Ile Tyr His Cys Lys His Lys Leu
225                 230

<210> SEQ ID NO 2
<211> LENGTH: 452
<212> TYPE: PRT
<213> ORGANISM: Artificial
<220> FEATURE:
<223> OTHER INFORMATION: Mouse/human chimeric

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

-continued

```
Gly Arg Ile Asp Pro Tyr Asp Ser Glu Thr His Tyr Ala Gln Lys Leu
     50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Gly Gly Tyr Asp Phe Asp Val Gly Thr Leu Tyr Trp Phe Phe
            100                 105                 110
Asp Val Trp Gly Gln Gly Thr Thr Val Thr Val Ser Ser Ala Ser Thr
            115                 120                 125
Lys Gly Pro Ser Val Phe Pro Leu Ala Pro Cys Ser Arg Ser Thr Ser
130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
            195                 200                 205
Asn Val Asp His Lys Pro Ser Asn Thr Lys Val Asp Lys Arg Val Glu
210                 215                 220
Ser Lys Tyr Gly Pro Pro Cys Pro Pro Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
            275                 280                 285
Val His Asn Ala Lys Thr Lys Pro Arg Glu Glu Gln Phe Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
            355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
            435                 440                 445
Ser Leu Gly Lys
    450
```

```
<210> SEQ ID NO 3
<211> LENGTH: 452
<212> TYPE: PRT
<213> ORGANISM: Artificial
<220> FEATURE:
<223> OTHER INFORMATION: Mouse/human chimeric

<400> SEQUENCE: 3
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Glu |
| 1 | | | | 5 | | | | | 10 | | | | | 15 | |
| Ser | Leu | Lys | Ile | Ser | Cys | Lys | Gly | Ser | Gly | Tyr | Ser | Phe | Thr | Ser | Tyr |
| | | | 20 | | | | | 25 | | | | | 30 | | |
| Trp | Met | Asn | Trp | Val | Arg | Gln | Met | Pro | Gly | Lys | Gly | Leu | Glu | Trp | Met |
| | | 35 | | | | | 40 | | | | | 45 | | | |
| Gly | Arg | Ile | Asp | Pro | Tyr | Asp | Ser | Glu | Thr | His | Tyr | Ser | Pro | Ser | Phe |
| 50 | | | | | 55 | | | | | 60 | | | | | |
| Gln | Gly | Gln | Val | Thr | Ile | Ser | Ala | Asp | Lys | Ser | Ile | Ser | Thr | Ala | Tyr |
| 65 | | | | | 70 | | | | | 75 | | | | | 80 |
| Leu | Gln | Trp | Ser | Ser | Leu | Lys | Ala | Ser | Asp | Thr | Ala | Met | Tyr | Tyr | Cys |
| | | | | 85 | | | | | 90 | | | | | 95 | |
| Ala | Arg | Gly | Gly | Tyr | Asp | Phe | Asp | Val | Gly | Thr | Leu | Tyr | Trp | Phe | Phe |
| | | | 100 | | | | | 105 | | | | | 110 | | |
| Asp | Val | Trp | Gly | Gln | Gly | Thr | Thr | Val | Thr | Val | Ser | Ser | Ala | Ser | Thr |
| | | 115 | | | | | 120 | | | | | 125 | | | |
| Lys | Gly | Pro | Ser | Val | Phe | Pro | Leu | Ala | Pro | Cys | Ser | Arg | Ser | Thr | Ser |
| 130 | | | | | 135 | | | | | 140 | | | | | |
| Glu | Ser | Thr | Ala | Ala | Leu | Gly | Cys | Leu | Val | Lys | Asp | Tyr | Phe | Pro | Glu |
| 145 | | | | | 150 | | | | | 155 | | | | | 160 |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |
| Val | Val | Thr | Val | Pro | Ser | Ser | Ser | Leu | Gly | Thr | Lys | Thr | Tyr | Thr | Cys |
| | | 195 | | | | | 200 | | | | | 205 | | | |
| Asn | Val | Asp | His | Lys | Pro | Ser | Asn | Thr | Lys | Val | Asp | Lys | Arg | Val | Glu |
| 210 | | | | | 215 | | | | | 220 | | | | | |
| Ser | Lys | Tyr | Gly | Pro | Pro | Cys | Pro | Pro | Cys | Pro | Ala | Pro | Glu | Phe | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| Gln | Glu | Asp | Pro | Glu | Val | Gln | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Phe | Asn | Ser | Thr |
| 290 | | | | | 295 | | | | | 300 | | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Gly | Leu | Pro | Ser | Ser |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Gln | Glu | Glu | Met | Thr | Lys | Asn | Gln | Val |
| | | 355 | | | | | 360 | | | | | 365 | | | |

-continued

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 4
<211> LENGTH: 452
<212> TYPE: PRT
<213> ORGANISM: Artificial
<220> FEATURE:
<223> OTHER INFORMATION: Mouse/human chimeric

<400> SEQUENCE: 4

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 5
<211> LENGTH: 452
<212> TYPE: PRT
<213> ORGANISM: Artificial
<220> FEATURE:
<223> OTHER INFORMATION: Mouse/human chimeric

<400> SEQUENCE: 5

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Asn Trp Val Gln Gln Ala Pro Gly Lys Gly Leu Glu Trp Met
        35                  40                  45

Gly Arg Ile Asp Pro Tyr Asp Ser Glu Thr His Tyr Ala Glu Lys Phe
    50                  55                  60

Gln Gly Arg Val Thr Ile Thr Ala Asp Thr Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Cys Pro Ala Pro Glu Phe Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 6
<211> LENGTH: 452
<212> TYPE: PRT
<213> ORGANISM: Artificial
<220> FEATURE:
<223> OTHER INFORMATION: Mouse/human chimeric

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Phe
    50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                    85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 7
<211> LENGTH: 214
<212> TYPE: PRT
<213> ORGANISM: Artificial
<220> FEATURE:
<223> OTHER INFORMATION: Mouse/human chimeric
```

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 5
<212> TYPE: PRT
<213> ORGANISM: Mus musculus

<400> SEQUENCE: 8

Ser Tyr Trp Met Asn
1               5

<210> SEQ ID NO 9
<211> LENGTH: 11
<212> TYPE: PRT
<213> ORGANISM: Mus musculus

<400> SEQUENCE: 9

Arg Ile Asp Pro Tyr Asp Ser Glu Thr His Tyr
1               5                   10

<210> SEQ ID NO 10
<211> LENGTH: 17
<212> TYPE: PRT
<213> ORGANISM: Artificial
<220> FEATURE:
<223> OTHER INFORMATION: Mouse/human chimeric

<400> SEQUENCE: 10

Arg Ile Asp Pro Tyr Asp Ser Glu Thr His Tyr Ser Pro Ser Phe Gln
1               5                   10                  15

Gly

<210> SEQ ID NO 11
<211> LENGTH: 17
<212> TYPE: PRT
<213> ORGANISM: Artificial
<220> FEATURE:
<223> OTHER INFORMATION: Mouse/human chimeric

<400> SEQUENCE: 11

Arg Ile Asp Pro Tyr Asp Ser Glu Thr His Tyr Ala Gln Lys Leu Gln
1               5                   10                  15

Gly

<210> SEQ ID NO 12
<211> LENGTH: 16
<212> TYPE: PRT
<213> ORGANISM: Mus musculus

<400> SEQUENCE: 12

Gly Gly Tyr Asp Phe Asp Val Gly Thr Leu Tyr Trp Phe Phe Asp Val
1               5                   10                  15

<210> SEQ ID NO 13
<211> LENGTH: 11
<212> TYPE: PRT
<213> ORGANISM: Mus musculus

<400> SEQUENCE: 13

Arg Ala Ser Glu Asn Ile Tyr Ser Tyr Leu Ala
1               5                   10

<210> SEQ ID NO 14
<211> LENGTH: 7
<212> TYPE: PRT
<213> ORGANISM: Mus musculus

<400> SEQUENCE: 14

Asn Ala Lys Thr Leu Ala Glu
1               5

<210> SEQ ID NO 15
<211> LENGTH: 9
<212> TYPE: PRT
<213> ORGANISM: Mus musculus

<400> SEQUENCE: 15

Gln His His Tyr Gly Thr Pro Arg Thr
1               5

<210> SEQ ID NO 16
<211> LENGTH: 119
<212> TYPE: PRT
<213> ORGANISM: Mus musculus

<400> SEQUENCE: 16

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

-continued

```
Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Ile Ser Ser Leu Arg Ser Glu Asp Thr Ala Met Tyr Tyr Cys
                85                  90                  95

Thr Arg His Gly Asp Tyr Pro Arg Phe Phe Asp Val Trp Gly Ala Gly
            100                 105                 110

Thr Thr Val Thr Val Ser Ser
        115

<210> SEQ ID NO 17
<211> LENGTH: 107
<212> TYPE: PRT
<213> ORGANISM: Mus musculus

<400> SEQUENCE: 17

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Ile
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys Arg
            100                 105
```

TREATMENT OF CANCERS USING ANTI-NKG2A AGENTS

CROSS-REFERENCE TO RELATED APPLICATIONS

This application is the U.S. national stage application of International Patent Application No. PCT/EP2015/074581, filed Oct. 23, 2015, which claims the benefit of U.S. Provisional Application No. 62/067,642, filed 23 Oct. 2014, which are incorporated herein by reference in their entirety; including any drawings.

REFERENCE TO SEQUENCE LISTING

The present application is being filed along with a Sequence Listing in electronic format. The Sequence Listing is provided as a file entitled "NKG2A-HN_ST25", created Oct. 20, 2015, which is 27 KB in size. The information in the electronic format of the Sequence Listing is incorporated herein by reference in its entirety.

FIELD OF THE INVENTION

This invention relates to the use of NKG2A-targeting agents for the treatment of cancers, notably head and neck cancers. This invention also provides advantageous combination regimens for use with NKG2A-targeting agents for the treatment of cancers.

BACKGROUND OF THE INVENTION

NK cell activity is regulated by a complex mechanism that involves both activating and inhibitory signals. Several distinct NK-specific receptors have been identified that play an important role in the NK cell mediated recognition and killing of HLA Class I deficient target cells. Natural Cytotoxicity Receptors (NCRs) refer to a class of activating receptor proteins, and the genes expressing them, that are specifically expressed in NK cells. Examples of NCRs include NKp30, NKp44, and NKp46 (see, e.g., Lanier (2001) Nat Immunol 2:23-27, Pende et al. (1999) J Exp Med. 190:1505-1516, Cantoni et al. (1999) J Exp Med. 189:787-796, Sivori et al (1997) J. Exp. Med. 186:1129-1136, Pessino et al. (1998) J Exp Med. 188(5):953-60; Mandelboim et al. (2001) Nature 409:1055-1060, the entire disclosures of which are herein incorporated by reference). These receptors are members of the Ig superfamily, and their cross-linking, induced by specific mAbs, leads to a strong NK cell activation resulting in increased intracellular $Ca^{++}$ levels, triggering of cytotoxicity, and lymphokine release, and an activation of NK cytotoxicity against many types of target cells.

CD94/NKG2A is an inhibitory receptor found on subsets of natural killer cells (NK cells), Natural Killer T cells (NKT cells) and T cells ($\alpha/\beta$ and $\gamma/\delta$). CD94/NKG2A restricts cytokine release and cytotoxic responses of aforementioned lymphocytes toward cells expressing the CD94/NKG2A-ligand HLA-E (see, e.g., WO99/28748). HLA-E has also been found to be secreted in soluble form by certain tumor cells (Derre et al., J Immunol 2006; 177:3100-7) and activated endothelial cells (Coupe) et al., Blood 2007; 109: 2806-14). Antibodies that inhibit CD94/NKG2A signalling may increase the cytokine release and cytolytic activity of lymphocytes toward HLA-E positive target cells, such as responses of CD94/NKG2A-positive NK cells toward virally infected cells. Therefore, therapeutic antibodies that inhibit CD94/NKG2A but that do not provoke the killing of CD94/NKG2A-expressing cells (i.e. non-depleting antibodies) may induce control of tumor-growth in cancer patients.

In addition, certain lymphomas such as, e.g., NK-lymphomas, are characterized by CD94/NKG2A expression. In such patients, therapeutic antibodies that target and kill CD94/NKG2A-expressing cells (i.e. depleting antibodies) may be able to eradicate tumor cells via antibody-dependent cellular cytotoxicity (ADCC) or complement-dependent cytotoxicity (CDC). Anti-NKG2A antibodies have also been suggested for use in treating autoimmune or inflammatory diseases (see, e.g., US20030095965, WO2006070286).

Various antibodies against NKG2A have been described in the art. WO2008/009545 describes humanized anti-NKG2A antibody Z270 while WO2009/092805 describes humanized anti-NKG2A antibody Z199. Vance et al. (J Exp Med 1999; 190: 1801-12) refers to rat anti-murine NKG2-antibody 20D5 (now commercially available via BD Biosciences Pharmingen, Catalog No. 550518, USA); and U.S. patent application publication 20030095965 describes murine antibody 3S9, which purportedly binds to NKG2A, NKG2C and NKG2E.

Head and neck squamous cell carcinoma (HNSCC) has an incidence of 600,000 cases per year and mortality rate of 50%. The major risk factors for HNSCC are tobacco use, alcohol consumption, and infection with human papilloma virus (HPV). Despite advances in knowledge of its epidemiology and pathogenesis, the survival rates for many types of HNSCC have improved little over the past forty years. The overall 5-year survival rate of HNSCC patients is only about 50%. Tobacco, alcohol consumption and viral agents are the major risk factors for development of HNSCC. These risk factors, together with genetic susceptibility, result in the accumulation of multiple genetic and epigenetic alterations in a multistep process of cancer development, and the understanding of such molecular carcinogenesis of HNSCC is being used for the development of targeted agents for treating HNSCC.

The idea of immunotherapy as a treatment for HNSCC has been in existence for decades, and attempts at treating HNSCC have involved targeting of tumor-specific antigens. Although improvements have been made in using such immune stimulatory treatment strategies for a variety of solid cancers, the use of these strategies for patients with head and neck squamous cell carcinoma (HNSCC) is lagging behind. Immunotherapeutic approaches for HNSCC are particularly complicated by the profound immune suppression that is induced by HNSCC, which potentially decreases the effectiveness of immune stimulatory efforts. A review of mechanisms by which HNSCC escapes the anti-tumor immune response, such as down-modulation of HLA class I, is provided in Duray et al. (2010) Clin. Dev. Immunol. Article ID 701657; 2010: 1-15

Consequently, there is a need in the art for improved benefit to patients having head and neck cancers.

SUMMARY OF THE INVENTION

The present invention arises, inter alia, from the discovery by the inventors that blockade of inhibitory receptor NKG2A using an anti-NKG2A antibody enables NK cells to effectively eliminate head and neck cancer cells. In particular, in head and neck cancer HLA-E is serving as a tumor escape mechanism, even when the cancer is being treated with other therapeutic agents, and including in HPV-positive patients. It is shown herein that head and neck cancer cells express HLA-E at levels which are causing inhibition of NKG2A-expression NK and/or T cells, and an anti-NKG2A antibody can reverse such inhibition. Moreover, even when head and neck cancer cells are treated with an EGFR inhibitor, tumor cell-expressed HLA-E continues to inhibit lysis by NK and/or T cells, and such inhibition can be reversed using an anti-NKG2A antibody.

Accordingly, in one embodiment, provided is a method for treating or preventing a head and neck cancer in an individual, the method comprising administering to an individual having a head and neck cancer a therapeutically active amount of a compound that neutralizes the inhibitory activity of a human NKG2A polypeptide. In one aspect, provided is a composition comprising a compound that neutralizes the inhibitory activity of a human NKG2A polypeptide, for use in the treatment or prevention of a head and neck squamous cell carcinoma (HNSCC). In one aspect the compound that neutralizes the inhibitory activity of a human NKG2A polypeptide is an antibody capable of binding NKG2A in bivalent manner. In one aspect the compound that neutralizes the inhibitory activity of a human NKG2A polypeptide is a non-depleting antibody (e.g. an antibody that lacks an Fc domain or that has an Fc domain with minimal or no binding to one or more Fcγ receptors). In one embodiment provided is a compound that inhibits a NKG2A polypeptide on NK and/or T cells and causes such NK and/or T cells to lyse HLA-E-expressing HNSCC cells, for use in the treatment or prevention of a HNSCC in an individual. Optionally the said treatment or prevention comprises administration of a compound that inhibits a NKG2A polypeptide to an individual having a HNSCC.

In one embodiment the cancer is an oropharyngeal tumor, a larynx tumor, a tumor of the oral cavity, or a tumor of the hypopharynx. In one embodiment, the HNSCC is an oral cavity SCC (OCSCC). OCSCC comprises squamous cell carcinoma of the lip, anterior ⅔ of the tongue, floor of the mouth, buccal mucosa, gingiva, hard palate and retromolar trigone.

In one embodiment the HNSCC is a metastatic cancer.

In one embodiment, the individual is human papillomavirus (HPV)-positive (e.g. characterized by the presence of human papillomavirus, positive for a HPV genotype associated with high cancer risk or poor cancer prognosis, positive for HPV16 genotype and/or positive for $P16^{INKa}$ expression).

In one embodiment, the individual has a head and neck cancer characterized by the presence of lymphocytes in the tumor environment (e.g., within tumor tissue and/or within tumor adjacent tissue).

In one embodiment, the anti-NKG2A antibody is administered in an amount that results in the neutralization of the inhibitory activity of human CD94/NKG2A in the human patient (in vivo), optionally wherein the anti-NKG2A antibody is administered at a dose that results in saturation of NKG2A polypeptides on peripheral blood NK and T lymphocytes for at least two weeks, optionally at least four weeks. In one embodiment, the anti-NKG2A antibody is administered at a dose of between 1 mg/kg and 10 mg/kg, optionally at about 4 mg/kg, optionally at about 10 mg/kg.

In one embodiment, a therapeutic regimen or course of therapy with the compound (e.g. antibody) that neutralizes the inhibitory activity of a human NKG2A polypeptide is administered to an individual having a head and neck cancer prior to surgery to remove cancer cells, i.e. as a preoperative treatment.

Optionally, HLA-E status of a cancer can be assessed prior to treatment with an anti-NKGA agent. In one embodiment provided is a method combining a HLA-E detection step to identify patients having HLA-E+HNSCC; these patients can thereafter be treated with an agent that neutralizes the inhibitory activity of a NKG2A polypeptide.

In one aspect, provided is a method for assessing whether an individual having an HNSCC is suitable for treatment with a compound that neutralizes the inhibitory activity of a human NKG2A polypeptide, the method comprising determining the HLA-E polypeptide status of malignant cells from the individual having a HNSCC, wherein a determination that the patient that HLA-E polypeptide expressed in malignant cells (e.g., prominently expressed; at a level that is increased compared to a reference level; at a level that is increased compared to that in the relevant tissue from healthy individuals, and/or at a level that corresponds to (at least) that of patients deriving benefit from an anti-NKG2A agent) indicates that such individual is suitable for treatment with a compound that neutralizes the inhibitory activity of a human NKG2A polypeptide.

In one embodiment of any of the therapeutic uses or HNSCC treatment or prevention methods herein, the treatment or prevention of a HNSCC in an individual comprises:
a) determining the HLA-E polypeptide status of malignant cells from the individual having a HNSCC, and
b) upon a determination that the patient that HLA-E polypeptide is expressed by malignant cells (e.g. at least at a value or proportion of tumor cells, at least medium or strong staining, etc.), administering to the individual a compound that neutralizes the inhibitory activity of a human NKG2A polypeptide.

In one embodiment of any of the therapeutic uses or HNSCC treatment or prevention methods herein, the treatment or prevention of a HNSCC in an individual comprises:
a) determining the HLA-E polypeptide status of malignant cells within the individual having a HNSCC, and
b) upon a determination that malignant cells express HLA-E polypeptide at a level that is at, or increased compared to, a reference level (e.g. increased compared to reference level for a healthy individual or a reference level for an individual not deriving benefit from an anti-NKG2A agent; at least at a reference level that corresponds to that of patients deriving benefit from an anti-NKG2A agent), administering to the individual a compound that neutralizes the inhibitory activity of a human NKG2A polypeptide.

In one embodiment of any of the methods, determining the HLA-E polypeptide status in step (a) comprises determining the level of expression of a HLA-E polypeptide of malignant cells in a biological sample and comparing the level to a reference level (e.g. a value, a proportion of HLA-E-positive malignant cells, and/or weak or absent staining, etc.) corresponding to a healthy individual or to an individual not deriving benefit from an anti-NKG2A agent. A determination that a biological sample expresses HLA-E polypeptide at a level that is increased compared to the reference level indicates that the patient has a head and neck cancer that can be treated with an agent that inhibits NKG2A.

In one embodiment of any of the methods, determining the HLA-E polypeptide status in step (a) comprises determining the level of expression of a HLA-E polypeptide of malignant cells in a biological sample and comparing the level to a reference level (e.g. a value, a proportion of HLA-E-positive malignant cells, and/or intermediate or strong cell surface staining, etc.). A determination that a biological sample expresses HLA-E polypeptide at a level that is at least at the reference level indicates that the patient has a head and neck cancer that can be treated with an agent that inhibits NKG2A.

In one embodiment of any of the methods, determining the HLA-E polypeptide status in step (a) comprises determining the level of expression of a HLA-E polypeptide of malignant cells in a biological sample and comparing the level to a reference level (e.g. a value, a proportion of HLA-E-positive malignant cells, and/or intermediate or strong cell surface staining, etc.) corresponding to an individual (e.g. having a cancer, a head and neck cancer) that derives benefit from treatment with an anti-NKG2A agent. A determination that a biological sample expresses HLA-E polypeptide at a level that is at least equal to a reference level corresponding to an individual who derives benefit from treatment with an anti-NKG2A agent indicates that the patient has a head and neck cancer that can be treated with an agent that inhibits NKG2A.

In one aspect of any embodiment, a determination that malignant cells from an individual have intermediate or strong HLA-E polypeptide expression (e.g. intermediate or strong staining in an immunohistochemistry detection assay) indicates that the patient has a head and neck cancer that the individual can be treated with an agent that inhibits NKG2A. In one aspect of any embodiment, a determination that a substantial proportion (e.g. at least about 25%, optionally at least 50%) of malignant cells from an individual have HLA-E polypeptide expression (e.g. intermediate or strong staining in an immunohistochemistry detection assay) indicates that the patient has a head and neck cancer that the individual can be treated with an agent that inhibits NKG2A. In one aspect of any embodiment, a determination that a substantial proportion (e.g. at least about 25%, optionally at least 50%) of malignant cells from an individual have HLA-E polypeptide expression (e.g. intermediate or strong staining in an immunohistochemistry detection assay) and the individual has a poor cancer prognosis (e.g., metastatic disease, HPV genotype, aggressive or advanced disease) indicates that the patient has a head and neck cancer that the individual can be treated with an agent that inhibits NKG2A. In one aspect of any embodiment, a determination that malignant cells from an individual have high HLA-E expression as evidenced by a strong signal diffusely expressed across all cells within the cellular subtype have HLA-E polypeptide expression (e.g. strong staining in an immunohistochemistry detection assay) indicates that the patient has a head and neck cancer that the individual can be treated with an agent that inhibits NKG2A.

In one embodiment, an anti-NKG2A agent can be advantageously used in a patient who is human papillomavirus (HPV)-positive (e.g. characterized by the presence of human papillomavirus in the patient, positive for a HPV genotype associated with high cancer risk or poor cancer prognosis, positive for HPV16 genotype and/or positive for P16INKa expression). In one embodiment, HPV infection causes increased expression on tumor cells of ligands that are recognized by activating receptors on NK and/or T cells (e.g. upregulation of NKG2D ligands, such as MICA or MICB), as well as increased expression of HLA-E on the surface of tumor cells, such that NKG2A-blocking therapy will be particularly effective in HPV positive individuals.

In one embodiment, provided is a method for treating or preventing a cancer in an individual who is HPV-positive, the method comprising administering to an HPV-positive individual having a cancer a therapeutically active amount of a compound that neutralizes the inhibitory activity of a human NKG2A polypeptide. In one embodiment, the cancer is a solid tumor, e.g. an advanced solid tumor. In one embodiment, the cancer is a head and neck cancer.

Optionally, HPV status of an individual can be assessed prior to treatment with an anti-NKG2A agent. In one embodiment, provided is a method for treating an individual having a head and neck cancer, the method comprising:
(a) determining whether the individual having a head and neck cancer is HPV-positive;
(b) if the individual is HPV-positive, treating the individual with (e.g. administering to the individual) a therapeutically active amount of a compound that neutralizes the inhibitory activity of a human NKG2A polypeptide.

In one embodiment, provided is a method for treating an individual having a cancer (e.g. use of a compound that neutralizes the inhibitory activity of a human NKG2A polypeptide for the treatment or prevention of a cancer in an individual), the method comprising:
a) determining whether the individual has a tumor characterized by the presence of lymphocytes in the tumor environment (e.g., within tumor tissue and/or within tumor adjacent tissue); and
b) upon a determination that the individual has a tumor characterized by the presence of lymphocytes in the tumor environment, administering to the individual a compound that neutralizes the inhibitory activity of a human NKG2A polypeptide. Optionally, the tumor is a solid tumor; optionally the tumor is a head and neck cancer.

In another embodiment, an individual having a head and neck cancer is HPV-negative. In one embodiment, provided is a method of treating an HPV-negative patient having a head and neck cancer, comprising administering to the individual a compound that neutralizes the inhibitory activity of a NKG2A polypeptide.

In one embodiment, the anti-NKG2A antibody is administered as single agent therapy. In one embodiment, the anti-NKG2A antibody is administered in combination treatment with one or more other anti-cancer agents.

In one embodiment, provided is a method for treating or preventing a cancer in an individual, the method comprising administering to an individual (a) a therapeutically active amount of a compound that inhibits a human NKG2A polypeptide and (b) a therapeutically active amount of a compound that binds and/or inhibits a human EGFR polypeptide. In one embodiment, the cancer is a HNSCC. In one embodiment, the compound that binds and/or inhibits a human EGFR is an anti-EGFR antibody.

In one embodiment, the anti-NKG2A antibody is administered in an effective amount that results in the neutralization of the inhibitory activity of human CD94/NKG2A in the human patient (in vivo), optionally wherein the anti-NKG2A antibody is administered at a dose that results in saturation of NKG2A polypeptides on peripheral blood NK and T lymphocyte for at least two weeks, optionally at least four weeks. In one embodiment, the anti-EGFR antibody is administered in an effective amount that elicits antibody-dependent cellular cytotoxicity toward human EGFR-expressing tumor cells in the human patient (in vivo). In one embodiment, the anti-EGFR antibody is administered in an effective amount that results in the neutralization of the activity of human EGFR in the human patient (in vivo). In one aspect, the combination is administered (or is for administration) according to a particular clinical dosage regimen, notably at a particular dose amount and according to a specific dosing schedule (e.g. a dose amount and/or according to a specific dosing schedule provided herein).

In one embodiment provided is a method for treatment or prevention of a cancer in an individual comprises:
a) determining the HLA-E polypeptide status of malignant cells within the individual having a cancer, b) determining the EGFR polypeptide status of malignant cells within the individual having a cancer and c) upon a determination that HLA-E and EGFR polypeptides are expressed on the surface of malignant cells from the individual at a level that is increased compared to the reference level, administering to the individual a therapeutic regimen that comprises a compound that neutralizes the inhibitory activity of a human NKG2A polypeptide and an agent that binds and/or inhibits EGFR.

In one embodiment of any of the therapeutic uses or HNSCC treatment or prevention methods herein, the treatment or prevention of a HNSCC in an individual comprises:

a) determining the HLA-E polypeptide status of malignant cells within the individual having a HNSCC, b) determining the EGFR polypeptide status of malignant cells within the individual having a HNSCC and c) upon a determination that HLA-E and EGFR polypeptides are expressed on the surface of malignant cells for the individual at a level that is increased compared to a reference level, administering to the individual a therapeutic regimen that comprises a compound that neutralizes the inhibitory activity of a human NKG2A polypeptide and an agent that binds and/or inhibits EGFR.

In any of the methods herein, determining polypeptide status or expression (e.g. HLA-E, NKG2A or EGFR) can be carried out directly (by detecting the polypeptide) or indirectly (e.g. by detecting a nucleic acid encoding the polypeptide).

The compound that neutralizes the inhibitory activity of a NKG2A polypeptide (anti-NKG2A agent) is a compound that increases the ability of an NKG2A-expressing NK and/or T cells to cause the death of the HLA-E-expressing cells. Optionally, the compound that neutralizes the inhibitory activity of a NKG2A polypeptide is a polypeptide, optionally an antibody (e.g. monoclonal antibody), that binds a NKG2A polypeptide.

In one embodiment, the anti-NKG2A agent reduces the inhibitory activity of NKG2A by blocking binding of its ligand, HLA-E, i.e., the anti-NKG2A agent interferes with the binding of NKG2A by HLA-E. The antibody having the heavy chains of any one of SEQ ID NOS: 2-6 and a light chain of SEQ ID NO: 7 is an example of such an antibody. In one embodiment, the anti-NKG2A agent reduces the inhibitory activity of NKG2A without blocking binding of its ligand, HLA-E, i.e., the anti-NKG2A agent is a non-competitive antagonist and does not interfere with the binding of NKG2A by HLA-E. The antibody having the heavy and light chain variable regions of SEQ ID NOS: 16 and 17 respectively is an example of such an antibody.

In one embodiment, the anti-NKG2A agent is antibody which binds with a significantly higher affinity to NKG2A than to one or more activating NKG2 receptors. For example, in one embodiment, the agent is antibody which binds with a significantly higher affinity to NKG2A than to NKG2C. In an additional or alternative embodiment, the agent is antibody which binds with a significantly higher affinity to NKG2A than to NKG2E. In an additional or alternative embodiment, the agent is antibody which binds with a significantly higher affinity to NKG2A than to NKG2H. The antibody having the heavy chains of any one of SEQ ID NOS: 2-6 and light chain of SEQ ID NO: 7 binds NKG2A without substantially binding to NKG2C, NKG2E or NKG2H.

In an additional or alternative embodiment, the anti-NKG2A agent competes with the antibody having the heavy chains of any one of SEQ ID NOS: 2-6 and light chain of SEQ ID NO: 7, and/or the antibody having the heavy and light chain variable regions of SEQ ID NOS: 16 and 17 respectively, in binding to CD94/NKG2A. The agent can be, e.g., a human or humanized anti-NKG2A antibody.

In one embodiment, the anti-NKG2A antibody is a humanized antibody having the heavy chains of any one of SEQ ID NOS: 2-6 and light chain of SEQ ID NO: 7. Exemplary complementarity-determining region (CDR) residues or sequences and/or sites for amino acid substitutions in framework region (FR) of such humanized antibodies having improved properties such as, e.g., lower immunogenicity, improved antigen-binding or other functional properties, and/or improved physicochemical properties such as, e.g., better stability, are provided.

In other embodiments, pharmaceutical compositions and kits are provided, as well as methods for using them.

These aspects are more fully described in, and additional aspects, features, and advantages will be apparent from, the description of the invention provided herein.

BRIEF DESCRIPTION OF THE DRAWINGS

FIG. 1A shows controls and K562 targets with low or high levels of surface HLA-E, and FIG. 1B demonstrates anti-NKG2A can restore lysis of HNSCC with endogenous HLA-E expression. This effect is only seen on NKG2A positive NK cells and is dependent on the level of expression of HLA-E.

FIG. 3A shows CD107 read out on controls with no target and with K562-HLA-E transfectants. Each healthy volunteer is represented by a different symbol: squares or circles. Crossed open symbols correspond to conditions where anti-NKG2A was replaced by 10 µg/mL hIgG4 isotypic control co-incubated with 0.1 µg/mL cetuximab. FIG. 3B shows CD107 read out on HNSCC cell lines. For each concentration of cetuximab, the symbols (squares of circles) for each concentration of anti-NKG2A correspond, from left to right, to 0 µg/ml, 0.1 µg/ml, 1 µg/ml, and 10 µg/ml.

DEFINITIONS

Figure 1A:
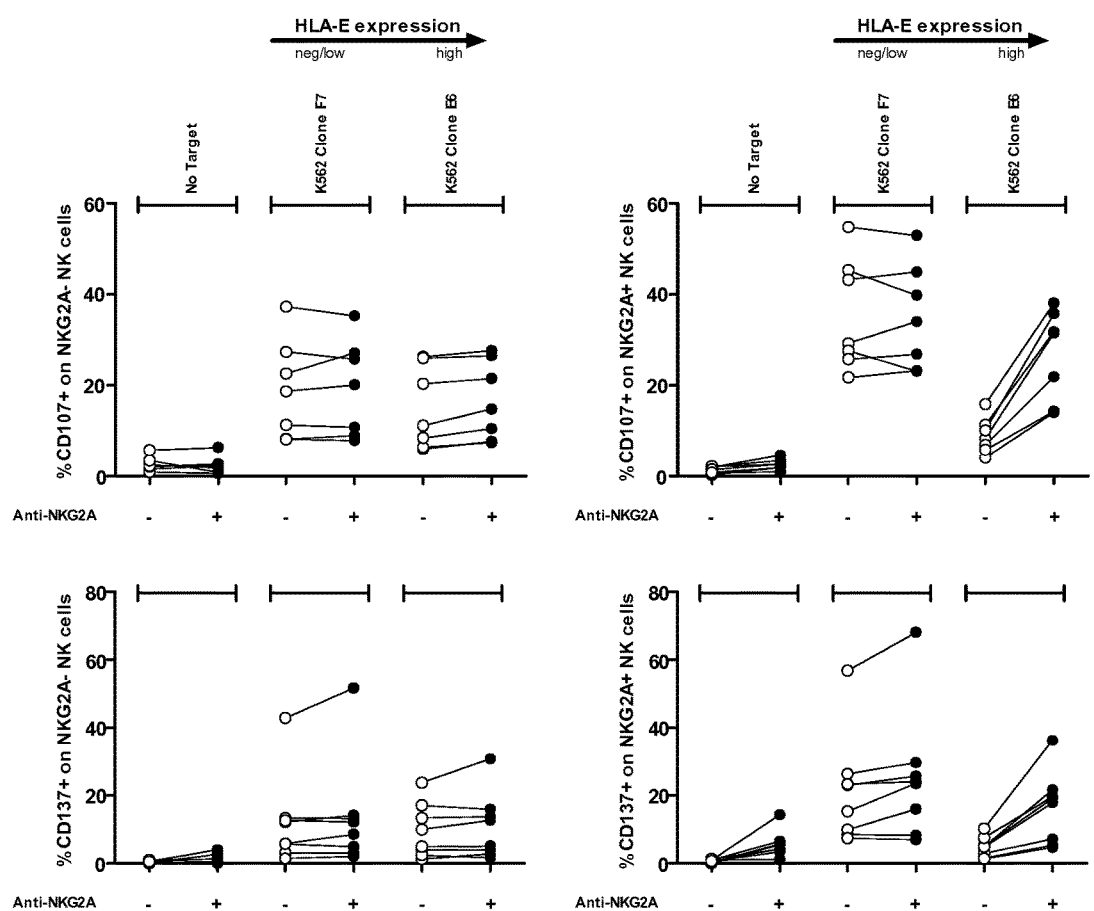
FIGS. 1A and 1B show ability of anti-NKG2A to enhance recognition of HNSCC cell lines by NK cells. CD107 (Top) and CD137 (Bottom) FACS read-outs on NKG2A-NK (left) or NKG2A+NK cells (right) are indicated, in presence of indicated target HNSCC cell lines and in presence or not of anti-NKG2A at a saturating dose of 10 µg/mL. The cell lines are ordered from left to right according to level of HLA-E surface expression. Each dot represents PBMC from a healthy volunteer.

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/δ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Also encompassed are any nucleic acid or protein sequences sharing one or more biological properties or functions with wild type, full length NKG2A, and sharing at least 70%, 80%, 90%, 95%, 96%, 97%, 98%, 99%, or higher nucleotide or amino acid identity. Human NKG2A comprises 233 amino acids in 3 domains, with a cytoplasmic domain comprising residues 1-70, a transmembrane region comprising residues 71-93, and an extracellular region comprising residues 94-233, of the following sequence:

```
                                         (SEQ ID NO: 1)
MDNQGVIYSDLNLPPNPKRQQRKPKGNKSSILATEQEITYAELNLQKASQ

DFQGND-KTYHCKDLPSAPEKLIVGILGIICLILMASVVTIVVIPSTLIQ

RHNNSSLNTRTQKARHCGH-CPEEWITYSNSCYYIGKERRTWEESLLACT

SKNSSLLSIDNEEEMKFLSIISPSS-WIGVFRNSSHHPWVTMNGLAFKHE

IKDSDNAELNCAVLQVNRLKSAQCGSSIIYHCKHKL.
```

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). The CD94/NKG2C and CD94/NKG2E receptors are activating receptors found on the surface of subsets of lymphocytes such as NK cells and T-cells.

HLA-E (OMIM 143010, the entire disclosure of which is herein incorporated by reference) is a nonclassical MHC molecule that is expressed on the cell surface and regulated by the binding of peptides, e.g., such as fragments derived from the signal sequence of other MHC class I molecules. Soluble versions of HLA-E have also been identified. In addition to its T-cell receptor binding properties, HLA-E binds subsets of natural killer (NK) cells, natural killer T-cells (NKT) and T cells (α/β and γ/δ), by binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E protects target cells from lysis by CD94/NKG2A+NK, T, or NKT cell clones. As used herein, "HLA-E" refers to any variant, derivative, or isoform of the HLA-E gene or encoded protein. Also encompassed are any nucleic acid or protein sequences sharing one or more biological properties or functions with wild type, full length HLA-E, and sharing at least 70%, 80%, 90%, 95%, 96%, 97%, 98%, 99%, or higher nucleotide or amino acid identity.

In the context of the present disclosure, "CD94/NKG2A positive lymphocyte" refers to cells of the lymphoid lineage (e.g. NK-, NKT- and T-cells) expressing CD94/NKG2A on the cell-surface, which can be detected by e.g. flow-cytometry using antibodies that specifically recognize a combined epitope on CD94 and NKG2A or an epitope on NKG2A alone. "CD94/NKG2A positive lymphocyte" also includes immortal cell lines of lymphoid origin (e.g. NKL, NK-92).

In the context of the present disclosure, "reduces the inhibitory activity of NKG2A", "neutralizes NKG2A" or "neutralizes the inhibitory activity of NKG2A" refers to a process in which CD94/NKG2A is inhibited in its capacity to negatively affect intracellular processes leading to lymphocyte responses such as cytokine release and cytotoxic responses. This can be measured for example in a NK- or T-cell based cytotoxicity assay, in which the capacity of a therapeutic compound to stimulate killing of HLA-E positive cells by CD94/NKG2A positive lymphocytes is measured. In one embodiment, an antibody preparation causes at least a 10% augmentation in the cytotoxicity of a CD94/NKG2A-restricted lymphocyte, preferably at least a 40% or 50% augmentation in lymphocyte cytotoxicity, or more preferably at least a 70% augmentation in NK cytotoxicity, referring to the cytotoxicity assays described. If an anti-NKG2A antibody reduces or blocks CD94/NKG2A interactions with HLA-E, it may increase the cytotoxicity of CD94/NKG2A-restricted lymphocytes. This can be evaluated, for example, in a standard 4-hour in vitro cytotoxicity assay using, e.g., NK cells that express CD94/NKG2A, and target cells that express HLA-E. Such NK cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). Chromium release and/or other parameters to assess the ability of the antibody to stimulate lymphocytes to kill target cells such as P815, K562 cells, or appropriate tumor cells are also disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference. The target cells are labeled with $^{51}$Cr prior to addition of NK cells, and then the killing is estimated as proportional to the release of $^{51}$Cr from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}$Cr-release cytotoxicity assay, CD94/NKG2A-expressing NK effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NK effector cells kill less efficiently HLA-E$^+$ LCL 721.221-Cw3 cells due to HLA-E-induced inhibitory signaling via CD94/NKG2A. When NK cells are pre-incubated with blocking anti-CD94/NKG2A antibodies according to the present invention in such a $^{51}$Cr-release cytotoxicity assay, HLA-E-expressing LCL 721.221-Cw3 cells are more efficiently killed, in an antibody-concentration-dependent fashion. The inhibitory activity (i.e. cytotoxicity enhancing potential) of an anti-NKG2A antibody can also be assessed in any of a number of other ways, e.g., by its effect on intracellular free calcium as described, e.g., in Sivori et al., J. Exp. Med. 1997; 186:1129-1136, the disclosure of which is herein incorporated by reference. Activation of NK cell cytotoxicity can be assessed for example by measuring an increase in cytokine production (e.g. IFN-γ production) or cytotoxicity markers (e.g. CD107 or CD137 mobilization). In an exemplary protocol, IFN-γ production from PBMC is assessed by cell surface and intracytoplasmic staining and analysis by flow cytometry after 4 days in culture. Briefly, Brefeldin A (Sigma Aldrich) is added at a final concentration of 5 μg/ml for the last 4 hours of culture. The cells are then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells are measured in supernatants using ELISA (GM-CSF: DuoSet Elisa, R&D Systems, Minneapolis, Minn., IFN-γ: OptEIA set, Pharmingen).

Whenever within this whole specification "treatment of HNSCC" or the like is mentioned with reference to an anti-NKG2A binding agent (e.g. antibody), there is meant: (a) method of treatment of HNSCC, said method comprising the step of administering (for at least one treatment) an anti-NKG2A binding agent (preferably in a pharmaceutically acceptable carrier material) to an individual, a mammal, especially a human, in need of such treatment, in a dose that allows for the treatment of HNSCC, (a therapeutically effective amount), preferably in a dose (amount) as specified herein; (b) the use of an anti-NKG2A binding agent for the treatment of HNSCC, or an anti-NKG2A binding agent for use in said treatment (especially in a human); (c) the use of an anti-NKG2A binding agent for the manufacture of a pharmaceutical preparation for the treatment of HNSCC, a method of using an anti-NKG2A binding agent for the manufacture of a pharmaceutical preparation for the treatment of HNSCC, comprising admixing an anti-NKG2A binding agent with a pharmaceutically acceptable carrier, or a pharmaceutical preparation comprising an effective dose of an anti-NKG2A binding agent that is appropriate for the treatment of HNSCC; or (d) any combination of a), b), and c), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of antibodies.

The term "specifically binds to" means that an antibody can bind preferably in a competitive binding assay to the binding partner, e.g. NKG2A, as assessed using either recombinant forms of the proteins, epitopes therein, or native proteins present on the surface of isolated target cells. Competitive binding assays and other methods for determining specific binding are well known in the art. For example binding can be detected via radiolabels, physical methods such as mass spectrometry, or direct or indirect fluorescent labels detected using, e.g., cytofluorometric analysis (e.g. FACScan). Binding above the amount seen with a control, non-specific agent indicates that the agent binds to the target. An agent that specifically binds NKG2A may bind NKG2A alone or NKG2A as a dimer with CD94.

When an antibody is said to "compete with" a particular monoclonal antibody, it means that the antibody competes with the monoclonal antibody in a binding assay using either recombinant molecules (e.g., NKG2A) or surface expressed molecules (e.g., NKG2A). For example, if a test antibody reduces the binding of an antibody having a heavy chain of any of SEQ ID NO: 2 and a light chain of SEQ ID NO: 7 to a NKG2A polypeptide or NKG2A-expressing cell in a binding assay, the antibody is said to "compete" respectively with such antibody.

The term "affinity", as used herein, means the strength of the binding of an antibody to an epitope. The affinity of an antibody is given by the dissociation constant Kd, defined as [Ab]×[Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor.

Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" and "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as naturally occurring amino acid polymers and non-naturally occurring amino acid polymer.

The term "recombinant" when used with reference, e.g., to a cell, or nucleic acid, protein, or vector, indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of Antibodies

The anti-NKG2A agent binds an extra-cellular portion of human CD94/NKG2A receptor and reduces the inhibitory activity of human CD94/NKG2A receptor expressed on the surface of a CD94/NKG2A positive lymphocyte. In one embodiment the agent competes with HLA-E in binding to CD94/NKG2A, i.e. the agent blocks the interaction between CD94/NKG2A and its ligand HLA-E. In another embodiment the agent does not compete with HLA-E in binding to CD94/NKG2A; i.e. the agent is capable of binding CD94/NKG2A simultaneously with HLA-E. The antibody may bind a combined epitope on CD94 and NKG2A or an epitope on NKG2A alone. In one embodiment, the antibody binds an epitope on NKG2A which at least partly overlaps with the HLA-E binding site.

In one aspect the anti-NKG2A agent is an antibody selected from a fully human antibody, a humanized antibody, and a chimeric antibody. In one aspect, the agent comprises a constant domain derived from a human IgG1, IgG2, IgG3 or IgG4 antibody. In one aspect, the agent is a fragment of an antibody selected from an IgA, an IgD, an IgG, an IgE and an IgM antibody. In one aspect, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the agent is a synthetic or semisynthetic antibody-derived molecule selected from a scFV, a dsFV, a minibody, a diabody, a triabody, a kappa body, an IgNAR; and a multispecific antibody.

Preferably, the anti-NKG2A antibodies do not demonstrate substantial specific binding to Fcγ receptors, e.g. CD16. Such antibodies may comprise constant regions of various heavy chains that are known not to bind Fc receptors. One such example is an IgG4 constant region. Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any human antibody type (e.g. IgG1, IgG2, IgG3 or IgG4) can be used in which the Fc portion is modified to minimize or eliminate binding to Fc receptors (see, e.g., WO03101485, the disclosure of which is herein incorporated by reference). Assays such as, e.g., cell based assays to assess Fc receptor binding are well known in the art, and are described in, e.g., WO03101485.

The present disclosure thus concerns antibodies or other agents binding to NKG2A. In one aspect, the antibody binds to NKG2A with a KD at least 100-fold lower than to human NKG2C and/or NKG2E.

In one aspect of the disclosure, the agent reduces CD94/NKG2A-mediated inhibition of a CD94/NKG2A-expressing lymphocyte by interfering with CD94/NKG2A signalling by, e.g., interfering with the binding of HLA-E by NKG2A, preventing or inducing conformational changes in the CD94/NKG2A receptor, and/or affecting dimerization and/or clustering of the CD94/NKG2A receptor.

In one aspect of the disclosure, the agent binds to an extracellular portion of NKG2A with a KD at least 100 fold lower than to NKG2C. In a further preferred aspect, the agent binds to an extracellular portion of NKG2A with a KD at least 150, 200, 300, 400, or 10,000 fold lower than to NKG2C. In another aspect of the disclosure, the agent binds to an extracellular portion of NKG2A with a KD at least 100 fold lower than to NKG2C, NKG2E and/or NKG2H molecules. In a further preferred aspect, the agent binds to an extracellular portion of NKG2A with a KD at least 150, 200, 300, 400, or 10,000 fold lower than to NKG2C, NKG2C and/or NKG2H molecules. This can be measured, for instance, in BiaCore experiments, in which the capacity of agents to bind the extracellular portion of immobilized CD94/NKG2A (e.g. purified from CD94/NKG2 expressing cells, or produced in a bio-system) is measured and compared to the binding of agents to similarly produced CD94/NKG2C and/or other CD94/NKG2 variants in the same assay. Alternatively, the binding of agents to cells that either naturally express, or over-express (e.g. after transient or stable transfection), CD94/NKG2A can be measured and compared to binding of cells expressing CD94/NKG2C and/or other CD94/NKG2 variants. Anti-NKG2A antibodies may optionally bind NKG2B, which is an NKG2A splice variant forming an inhibitory receptor together with CD94. In one embodiment, affinity can be measured using the methods disclosed in U.S. Pat. No. 8,206,709, for example by assessing binding to covalently immobilized NKG2A-CD94-Fc fusion protein by Biacore as shown in Example 8 of U.S. Pat. No. 8,206,709, the disclosure of which is incorporated herein by reference.

The antibody can, for example, have an $EC_{50}$ for binding (high affinity) to NKG2A-expressing cells of between 0.5-10 ng/ml, optionally 1-5 ng/ml, optionally 1-10 ng/ml, optionally 1-20 ng/ml, e.g. about 4 ng/ml. The NKG2A-expressing cells can be, for example, NKG2A-expressing cells in human PBMC. In one embodiment, the NKG2A-expressing cells are cells made to express CD94/NKG2A, for example Ba/F3 cells stably overexpressing CD94/NKG2A as shown in Example 13 of U.S. Pat. No. 8,206,709, the disclosure of which is incorporated by reference. In one embodiment, the antibody has binding affinity ($K_D$), optionally wherein binding affinity is bivalent, for a human NKG2A polypeptide of less than $10^{-9}$ M, optionally less than $10^{-10}$ M, or optionally less than $10^{-11}$M, optionally between $10^{-10}$ M and $10^{-12}$M, optionally between $10^{-10}$ M and $10^{-11}$M. Affinity can be assessed, for example, for binding to a single-chain NKG2A-CD94-mFc construct as described in U.S. Pat. No. 7,932,055, the disclosure of which is incorporated by reference.

The anti-NKG2A antibody can be a human or humanized antibody, for example comprising the respective VH and VL regions of the antibodies shown in the Table below.

| Antibody | VH | VL |
|---|---|---|
| VH6 | SEQ ID NO: 2 | SEQ ID NO: 7 |
| VH1 | SEQ ID NO: 3 | SEQ ID NO: 7 |
| VH5 | SEQ ID NO: 4 | SEQ ID NO: 7 |
| VH7 | SEQ ID NO: 5 | SEQ ID NO: 7 |
| VH8 | SEQ ID NO: 6 | SEQ ID NO: 7 |
| Z199 | SEQ ID NO: 16 | SEQ ID NO: 17 |

The anti-NKG2A antibody can be a human or humanized antibody, for example comprising a VH human acceptor framework from a human acceptor sequence selected from, e.g., VH1_18, VH5_a, VH5_51, VH1_f, VH1_46, and a JH6 J-segment, or other human germline VH framework sequences known in the art. The VL region human acceptor sequence may be, e.g., VKI_O2/JK4.

In one embodiment, the antibody is a humanized antibody based on antibody Z270. Different humanized Z270VH chains are shown in SEQ ID NOS: 2-6 (variable region domain amino acids underlined). Humanized Z270VH light chain is shown in SEQ ID NO: 7. HumZ270 antibody is also disclosed in U.S. Pat. No. 8,206,709 (the disclosure of which is incorporated herein by reference). HumZ270VH6 (SEQ ID NO: 3) is based on VH5_51; HumZ270VH1 (SEQ ID NO: 2) is based on VH1_18; humZ270VH5 (SEQ ID NO: 4) is based on VH5_a; humZ270VH7 (SEQ ID NO: 5) is based on VH1_f; and humZ270VH8 (SEQ ID NO: 6) is based on VH1_46; all with a JH6 J-segment. Each of these antibodies retains high affinity binding to NKG2A, with low likelihood of a host immune response against the antibody as the 6 C-terminal amino acid residues of the Kabat CDR-H2 of each of the humanized constructs are identical to the human acceptor framework. Using the alignment program VectorNTI, the following sequence identities between humZ270VH1 and humZ270VH5, -6, -7, and -8 were obtained: 78.2% (VH1 vs. VH5), 79.0% (VH1 vs. VH6), 88.7% (VH1 vs. VH7), and 96.0% (VH1 vs. VH8).

In one aspect, the agent comprises (i) a heavy chain variable region of any of SEQ ID NOS: 2-6, or an amino acid sequence at least 50%, 60%, 70%, 80%, 90%, 95%, 98% or 99% identical thereto, and (ii) a light chain variable region of SEQ ID NO: 7, or an amino acid sequence at least 50%, 60%, 70%, 80%, 90%, 95%, 98% or 99% identical thereto. In one aspect, the agent comprises (i) a heavy chain comprising the amino acid sequence of any of SEQ ID NOS: 2-6, or an amino acid sequence at least 50%, 60%, 70%, 80%, 90%, 95%, 98% or 99% identical thereto, and (ii) a light chain comprising the amino acid sequence of SEQ ID NO: 7, or an amino acid sequence at least 50%, 60%, 70%, 80%, 90%, 95%, 98% or 99% identical thereto. The antibody having the heavy chain comprising the sequence of any of SEQ ID NOS: 2-6 and a light chain comprising the sequence of SEQ ID NO: 7 neutralizes the inhibitory activity of NKG2A, but does not substantially bind the activating receptors NKG2C, NKGE or NKG2H. This antibody furthermore competes with HLA-E for binding to NKG2A on the surface of a cell. In one aspect, the agent comprises HCDR1, HCDR2 and/or HCDR3 sequences derived from the heavy chain having the amino acid sequence of any of SEQ ID NO: 2-6. In one aspect of the invention, the agent comprises LCDR1, LCDR2 and/or LCDR3 sequences derived from the light chain having the amino acid sequence of SEQ ID NO: 7.

Heavy Chains (Variable Regions Underlined)
VH1:

```
Heavy Chains (variable regions underlined)
VH1:
                                       (SEQ ID NO: 2)
QVQLVQSGAEVKKPGASVKVSCKASGYTFTSYWMNWVRQAPGQGLEWMGR

IDPYDSETHYA-QKLQGRVTMTTDTSTSTAYMELRSLRSDDTAVYYCARG

GYDFDVGTLYWFFDVWGQGTTVTVSSASTKGPSVFPLAPCSRSTSESTAA

LGCLVKDYFPEPVTVSWNSGALTSGVHTFPAVLQSSG LYS-LSSVVTVP

SSSLGTKTYTCNVDHKPSNTKVDKRVESKYGPPCPPCPAPEFLGGPSVFL

FPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLS

LSLGK

VH6:
                                       (SEQ ID NO: 3)
EVQLVQSGAEVKKPGESLKISCKGSGYSFTSYWMNWVRQMPGKGLEWMGR

IDPYD-SETHYSPSFQGQVTISADKSISTAYLQWSSLKASDTAMYYCARG

GYDFDVGTLYWFFDVWGQGTTVTVSSASTKGPSVFPLAPCSRSTSESTAA

LGCLVKDYFPEPVTVSWNSGALTSGVHTFPAVLQSSGLYSLSSVVTVPSS

SLGTKTYTCNVDHKPSNTKVDKRVESKYGPPCPPCPAPEFLGG-PSVFLF

PPKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSL

SLGK

VH5:
                                       (SEQ ID NO: 4)
EVQLVQSGAEVKKPGESLRISCKGSGYSFTSYWMNWVRQMPGKGLEWMGR

IDPYD-SETHYSPSFQGHVTISADKSISTAYLQWSSLKASDTAMYYCARG

GYDFDVGTLY-WFFDVWGQGTTVTVSSASTKGPSVFPLAPCSRSTSESTA

ALGCLVKDYFPEPVTVSWNSGALTSGVHTFPAVLQSSGLYSLSSVVTVPS

SSLGTKTYTCNVDHKPSNTKVDKRVESKYGPPCPPCPAPEFLGGPSVFLF

PPKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSL

SLGK

VH7:
                                       (SEQ ID NO: 5)
EVQLVQSGAEVKKPGATVKISCKVSGYTFTSYWMNWVQQAPGKGLEWMGR

IDPYDSETHYAEKFQGRVTITADTSTDTAYMELSSLRSEDTAVYYCATGG

YDFDVGTLYWFFDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK

VH8:
                                       (SEQ ID NO: 6)
QVQLVQSGAEVKKPGASVKVSCKASGYTFTSYWMNWVRQAPGQGLEWMGR

IDPYDSETHYAQKFQGRVTMTRDTSTSTVYMELSSLRSEDTAVYYCARGG

YDFDVGTLYWFFDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK
```

-continued

Light chain (SEQ ID NO: 7)
DIQMTQSPSSLSASVGDRVTITCRASENIYSYLAWYQQKPGKAPKLLIYN

AKTLAEGVPSRFSGSGSGTDFTLTISSLQPEDFATYYCQHHYGTPRTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In one aspect, the anti-NKG2A antibody is an antibody comprising a CDR-H1 corresponding to residues 31-35 of any of SEQ ID NOS: 2-6 (the amino acid sequence SYWMN (SEQ ID NO: 8)), a CDR-H2 corresponding to residues 50-60 (the amino acid sequence RIDPYDSETHY (SEQ ID NO: 9)) (optionally 50-66 when including the 6 terminal amino acids of human origin, i.e. the sequence RIDPYDSETHYSPSFQG (SEQ ID NO: 10) for the VH6 heavy chain, the sequence RIDPYDSETHYAQKLQG (SEQ ID NO: 11) for the VH1 heavy chain, etc.) of any of SEQ ID NOS: 2-6, and a CDR-H3 corresponding to residues 99-114 (95-102 according to Kabat) of any of SEQ ID NOS: 2-6 (the amino acid sequence GGYDFDVGTLYWFFDV (SEQ ID NO: 12)). In one embodiment, the CDR-H2 corresponds to residues 50-66 of any of SEQ ID NOS: 2-6. Optionally, a CDR may comprise one, two, three, four, or more amino acid substitutions.

In one aspect, the anti-NKG2A antibody is an antibody comprising a CDR-L1 corresponding to residues 24-34 of SEQ ID NO: 7 (the amino acid sequence RASENIYSYLA (SEQ ID NO: 13)), a CDR-L2 corresponding to residues 50-56 of SEQ ID NO: 7 (the amino acid sequence NAKTLAE (SEQ ID NO: 14)), and a CDR-L3 corresponding to residues 89-97 of SEQ ID NO: 7 (the amino acid sequence QHHYGTPRT (SEQ ID NO: 15)). Optionally, a CDR may comprise one, two, three, four, or more amino acid substitutions.

In one aspect, the anti-NKG2A antibody is an antibody comprising a CDR-H1 corresponding to residues 31-35 of any of SEQ ID NOS: 2-6, a CDR-H2 corresponding to residues 50-60 (optionally 50-66) of any of SEQ ID NOS: 2-6, and a CDR-H3 corresponding to residues 99-114 (95-102 according to Kabat) of any of SEQ ID NOS: 2-6, a CDR-L1 corresponding to residues 24-34 of SEQ ID NO: 7, a CDR-L2 corresponding to residues 50-56 of SEQ ID NO: 7, and a CDR-L3 corresponding to residues 89-97 of SEQ ID NO: 7.

In one aspect, the agent is a fully human antibody which has been raised against the CD94/NKG2A epitope to which any of the aforementioned antibodies bind.

It will be appreciated that, while the aforementioned antibodies can be used, other antibodies can be prepared. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. Most preferably, the epitope is the epitope specifically recognized by antibody having the heavy chain of any of SEQ ID NOS: 2-6 and the light chain of SEQ ID NO: 7.

In one aspect, the agent comprises HCDR1, HCDR2 and/or HCDR3 sequences derived from the VH having the amino acid sequence of SEQ ID NO: 16. In one aspect of the disclosure, the agent comprises LCDR1, LCDR2 and/or LCDR3 sequences derived from the VL having the amino acid sequence of SEQ ID NO: 17. In one aspect, the agent comprises HCDR1, HCDR2 and/or HCDR3 sequences derived from the VH having the amino acid sequence of SEQ ID NO: 16, and LCDR1, LCDR2 and/or LCDR3 sequences derived from the VL having the amino acid sequence of SEQ ID NO: 17. The antibody having the heavy chain of SEQ ID NO: 16 and a light chain of SEQ ID NO: 17 neutralizes the inhibitory activity of NKG2A, and also binds the activating receptors NKG2C, NKGE or NKG2H. The antibody does not compete with HLA-E for binding to NKG2A on the surface of a cell (i.e. it is a non-competitive antagonist of NKG2A).

(SEQ ID NO: 16)
EVQLVESGGGLVKPGGSLKLSCAASGFTFSSYAMSWVRQSPEKRLEWVAE
ISSGGSYTYYPDTVTGRFTISRDNAKNTLYLEISSLRSEDTAMYYCTRHG
DYPRFFDVWGAGTTVTVSS (SEQ ID NO: 17)
QIVLTQSPALMSASPGEKVTMTCSASSSVSYIYWYQQKPRSSPKPWIYLT
SNLASGVPARFSGSGSGTSYSLTISSMEAEDAATYYCQQWSGNPYTFGGG
TKLEIKR

In one aspect, the agent comprises amino acid residues 31-35, 50-60, 62, 64, 66, and 99-108 of the variable-heavy ($V_H$) domain (SEQ ID NO: 16) and amino acid residues 24-33, 49-55, and 88-96 of the variable-light ($V_L$) domain (SEQ ID NO: 17), optionally with one, two, three, four, or more amino acid substitutions.

In one aspect, the agent is a fully human antibody which has been raised against the CD94/NKG2A epitope to which any of the aforementioned antibodies bind.

It will be appreciated that, while the aforementioned antibodies can be used, other antibodies can recognize and be raised against any part of the NKG2A polypeptide so long as the antibody causes the neutralization of the inhibitory activity of NKG2A. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. In one embodiment, the epitope is the epitope specifically recognized by antibody having the heavy chain of any of SEQ ID NOS: 2-6 and the light chain of SEQ ID NO: 7.

In one aspect, the agent competes with humZ270 antibody disclosed in U.S. Pat. No. 8,206,709 (the disclosure of which is incorporated herein by reference) in binding to the extracellular portion of human CD94/NKG2A receptor. In one aspect, the agent competes with humanized Z199 antibody disclosed in U.S. Pat. No. 8,796,427 (the disclosure of which is incorporated herein by reference) in binding to the extracellular portion of human CD94/NKG2A receptor. Competitive binding can be measured, for instance, in BiaCore experiments, in which the capacity of agents is measured for binding the extracellular portion of immobilized CD94/NKG2A receptor (e.g. purified from CD94/NKG2 expressing cells, or produced in a bio-system) saturated with humZ270. Alternatively, the binding of agents to cells is measured that either naturally express, or over-express (e.g. after transient or stable transfection), CD94/NKG2A receptor, and which have been pre-incubated with saturating doses of Z270. In one embodiment, competitive binding can be measured using the methods disclosed in U.S. Pat. No. 8,206,709, for example by assessing binding to Ba/F3-CD94-NKG2A cells by flow cytometry as shown in Example 15 of U.S. Pat. No. 8,206,709, the disclosure of which is incorporated herein by reference.

Antibody Formulations

An anti-NKG2A agent such as an antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water. In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment.

In a further embodiment, the formulation further comprises a pharmaceutically acceptable preservative. In a further embodiment, the formulation further comprises an isotonic agent. In a further embodiment, the formulation also comprises a chelating agent. In a further embodiment the formulation further comprises a stabilizer. In a further embodiment, the formulation further comprises a surfactant. For convenience reference is made to Remington: The Science and Practice of Pharmacy, 19$^{th}$ edition, 1995.

It is possible that other ingredients may be present in the peptide pharmaceutical formulation. Such additional ingredients may include wetting agents, emulsifiers, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation.

Pharmaceutical compositions containing an antibody may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for example through the conjunctiva, urethral, and parenteral to patients in need of such a treatment.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab), Xolair (Omalizumab), Bexxar (Tositumomab), Campath (Alemtuzumab), Zevalin, Oncolym and similar formulations may be used with the antibodies of the disclosure. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Diagnosis and Treatment of Malignancies

Described are methods useful in the diagnosis, prognosis, monitoring, treatment and prevention of head and neck cancer in an individual. A HNSCC is a squamous cell or basaloid tumor that arises in the head or neck region and includes tumors of the nasal cavity, sinuses, lips, mouth and oral cavity, salivary glands, pharynx, or larynx. Anti-NKG2A agents can be particularly useful for example in the treatment of oropharyngeal tumors, tumors of the larynx, tumors of the oral cavity and tumors of the hypopharynx. Such tumors are routinely identified by practitioners in the field of oncology, such as physicians, medical oncologists, histopathologists and oncological clinicians. Treatment of HNSCC also includes the treatment of a premalignant lesion thereof. The premalignant lesions of HNSCC may include for example, dysplasia, hyperplasia, leukoplakia, erythroplakia, or hairy tongue.

A compound (e.g. antibody) that neutralizes the inhibitory activity of a human NKG2A polypeptide can be administered to an individual having a head and neck cancer who has not received surgery to remove cancer cells, or who has not in the current period received such surgery. However it will be appreciated that the compound can also be administered to a patient who has received, or who is undergoing, surgery to remove cancer cells. Where the anti-NKG2A compound is administered to an individual who has not received surgical intervention to remove cancer cells (e.g. to remove HNSCC cells), the NKG2A-binding compound can for example be administered approximately 0 to 30 days prior to surgery. In one embodiment, at least one (e.g. one, two, three, four or more) administration cycle of treatment with anti-NKG2A compound is administered prior to surgery. In one embodiment, the administration cycle is between 2 weeks and 8 weeks.

A patient having a head and neck cancer can be treated with the anti-NKG2A agents with or without a prior detection step to assess expression of HLA-E on the surface of tumor cells. Advantageously, the treatment methods can comprise a step of detecting an HLA-E nucleic acid or polypeptide in a biological sample of a tumor (e.g. on a tumor cell) from an individual. A determination that a biological sample expresses HLA-E (e.g. prominently expresses; expresses HLA-E at a high level, high intensity of staining with an anti-HLA-E antibody, compared to a reference) indicates that the patient has a head and neck cancer that may have a strong benefit from treatment with an agent that inhibits NKG2A. In one embodiment, the method comprises determining the level of expression of a HLA-E nucleic acid or polypeptide in a biological sample and comparing the level to a reference level (e.g. a value, weak cell surface staining, etc.) corresponding to a healthy individual or to an individual that does not benefit from treatment with an agent that inhibits NKG2A. A determination that a biological sample expresses HLA-E nucleic acid or polypeptide at a level that is increased compared to the reference level indicates that the patient has a head and neck cancer that can be treated with an agent that inhibits NKG2A. Optionally, detecting a HLA-E polypeptide in a biological sample comprises detecting HLA-E polypeptide expressed on the surface of a malignant HNSCC cell. In one embodiment, a determination that a biological sample prominently expresses HLA-E nucleic acid or polypeptide indicates that the patient has a head and neck cancer that can be treated with an agent that inhibits NKG2A. "Prominently expressed", when referring to a HLA-E polypeptide, means that the HLA-E polypeptide is expressed in a substantial number of tumor cells taken from a given patient. While the definition of the term "prominently expressed" is not bound by a precise percentage value, in some examples a receptor said to be "prominently expressed" will be present on at least 30%, 40%, 50°%, 60%, 70%, 80%, or more of the HNSCC cells taken from a patient.

Determining whether an individual has head and neck cancer cells that express an HLA-E polypeptide can for example comprise obtaining a biological sample (e.g. by performing a biopsy) from the individual that comprises head and neck cancer cells, bringing said cells into contact with an antibody that binds an HLA-E polypeptide, and detecting whether the cells express HLA-E on their surface. Optionally, determining whether an individual has head and neck cancer cells that express HLA-E comprises conducting an immunohistochemistry assay. Optionally determining whether an individual has head and neck cancer cells that express HLA-E comprises conducting a flow cytometry assay.

A patient having a head and neck cancer can be treated with the anti-NKG2A agents with or without a prior detection step to assess whether the patient (or the patient's tumor) is HPV positive. In one aspect, provided is a method of predicting whether a patient having a tumor will benefit from treatment with an anti-NKG2A agent. In one embodiment the method comprises determining whether the patient is HPV positive.

In one embodiment, the step of determining whether an individual having a HNSCC is HPV-positive includes detecting or identifying an HPV molecule in the subject, e.g., in a sample from the subject. In one embodiment, the HPV molecule is an HPV nucleic acid or HPV protein in the subject, e.g., the sample. In some embodiments, an HPV nucleic acid is identified by in situ hybridization (ISH), PCR, Northern blot analysis, or sequencing of nucleic acids in the sample. HPV protein can be identified, e.g., immunohistochemistry (IHC), by Western blot analysis. In one embodiment, HPV is detected by IHC to detect p16 protein (encoded by CDKN2A). A sample from a subject can be, for example, a blood or serum sample, or a urine sample, or a tissue sample, such as a tumor tissue sample (such as from a biopsy), or a buccal swab. The sample can be fresh or frozen. In one embodiment, an individual who is HPV-positive is positive for type 16 HPV, or optionally type 18, 31 and 33 HPV. Optionally, the step of determining whether an individual having a HNSCC is HPV-positive comprises detecting type 16 HPV, and/or type 18, 31 and/or 33 HPV.

Generally any suitable HPV assay methodology can be used. Examples of FDA-approved HPV assays include Digene Hybrid Capture 2 High-Risk HPV DNA Test (Qiagen Corp), an in vitro microplate assay based on signal-amplified nucleic acid hybridization that uses chemiluminescence for the qualitative detection of 18 types of human papillomavirus (HPV) DNA in cervical specimens. Another example is the Cervista™ HPV test from Third Wave Technologies. Another example is the cobas HPV Test from Roche Molecular Systems, Inc., CA. A further example is the APTIMA® HPV Assay from Gen-Probe, Inc. A patient who is HPV-positive can then for example be designated as an individual suited for treatment with an anti-NKG2A agent, or designated as a responder for treatment with an anti-NKG2A agent, and optionally can be further treated with an anti-NKG2A agent.

Optionally, an individual is assessed for the presence of one or more HNSCC-associated genetic markers. An HNSCC-associated gene may have an aberrant loss-of-function or gain-of-function in that or associated genes. Anti-NKG2A agents may be useful independently of mutations in HNSCC-associated genes and/or may be useful in enhancing the anti-tumor response in individuals having poor cancer prognosis, e.g. on the basis of one or more genetic markers. Thus, anti-NKG2A agents can be used to treat a patient having (or lacking) a HNSCC with a mutation in a HNSCC-associated gene, e.g. a gene selected from the group consisting of P13 Kinase (P13K), PIK3CA, PIK3CG, TP63, CCND1, CCNE1, MYC, YAP1, HRAS, NOTCH1, NOTCH 2, NOTCH 3, IRF6, CDKN2A, TP53, CASP8, PTEN, FAT1, RIPK4, EZH1, EZH2, MED1, MLL2, CDH1, FBXW7, PCLO, RIMS2, RBI, NSD1, EP300 and NFE2L2. Exemplary aberrant gain-of-function HNSCC genes may include TP63, CCND1, CCNE1, MYC, YAP1, HRAS, PIK3CA, PIK3CG or NFE2L2. Exemplary aberrant loss-of-function HNSCC genes may include NOTCH1, NOTCH 2, NOTCH 3, IRF6, CDKN2A, TP53, CASP8, PTEN, FAT1, RIPK4, EZH1, EZH2, MED1, MLL2, CDH1, FBXW7, PCLO, RIMS2, RBI, NSD1 or EP300. HNSCC-associated genes are also described in Stransky et al., "The Mutational Landscape of Head and Neck Squamous Cell Carcinoma", Science, Vol 333, 26 Aug. 2011, the contents of which are incorporated by reference herein in their entirety.

In one exemplary aspect, provided is method of reducing progression of HNSCC in a mammalian host, (e.g., a human patient) having a detectable level of cancer cells comprising administering an anti-NKG2A agent (e.g. an anti-NKG2A antibody), an anti-NKG2A antibody composition, or a related composition (e.g., a nucleic acid encoding an anti-NKG2A antibody), in an amount sufficient to detectably reduce the progression of the HNSCC in the host.

Suitable treatment protocols for treating a human having cancer include, for example, administering to the patient an effective amount of an antibody that neutralizes the inhibitory activity of human NKG2A, wherein the method comprises at least one administration cycle in which at least one dose of the anti-NKG2A antibody is administered at a dose of 1-10 mg/kg body weight. In one embodiment, the administration cycle is between 2 weeks and 8 weeks.

In one embodiment, the method comprises at least one administration cycle, wherein the cycle is a period of eight weeks or less, wherein for each of the at least one cycle, two, three or four doses of the anti-NKG2A antibody are administered at a dose of 1-10 mg/kg body weight.

In one embodiment, anti-NKG2A is administered in an amount effective to saturate NKG2A receptors on lymphocytes for at least one week, two weeks, three weeks or four weeks. In certain embodiments, a dose (e.g. each dose) of the anti-NKG2A antibody is administered at about 1, 2, 3, 4, 5, 6, 7, 8, 9 or 10 mg/kg.

In one aspect of any of the embodiments herein, the anti-NKG2A antibody is administered once about every two or four weeks.

Delivering anti-NKG2A antibodies to a subject (either by direct administration or expression from a nucleic acid therein, such as from a pox viral gene transfer vector comprising anti-NKG2A antibody-encoding nucleic acid sequence(s)) and practicing the other methods herein can be used to reduce, treat, prevent, or otherwise ameliorate any suitable aspect of cancer progression (notably HNSCC progression). The methods can be particularly useful in the reduction and/or amelioration of tumor growth (e.g. percentage (tumor cells compared to healthy T cells), number of tumor cells in circulation), and any parameter or symptom associated therewith (e.g. biomarkers). Methods that reduce, prevent, or otherwise ameliorate such aspects of cancer progression, independently and collectively, are advantageous features.

In another aspect, provided is a method of reducing the risk of cancer progression, reducing the risk of further cancer progression in a cell population that has undergone initiation, and/or providing a therapeutic regimen for reducing cancer progression in a human patient, which comprises administering to the patient one or more first treatments (e.g. induction therapy, such as a chemotherapeutic agent) in an amount and regimen sufficient to achieve a response (partial or complete response), and then administering an amount of an anti-NKG2A antibody or related composition (or applying a combination administration method) to the patient.

In a further aspect, provided is a method of promoting remission of a HNSCC in a mammalian host, such as a human patient, comprising administering a composition comprising an anti-NKG2A antibody, to the host, so as to promote HNSCC remission in the host.

In an even further aspect, provided is a method for reducing the risk of developing a HNSCC, reducing the time to onset of a cancerous condition, and/or reducing the severity of a HNSCC diagnosed in the early stages, comprising administering to a host a prophylactically effective amount of an anti-NKG2A antibody or related composition so as to achieve the desired physiological effect(s).

In a further aspect, provided is a method of increasing the likelihood of survival over a relevant period of a human patient diagnosed with HNSCC. In another aspect, provided is a method for improving the quality of life of a HNSCC patient comprising administering to the patient a composition in an amount effective to improve the quality of life thereof. In a further aspect, methods described herein can be applied to significantly reduce the number of HNSCC cells in a vertebrate host, such that, for example, the total number of HNSCC cells is reduced. In a related sense, provided is a method for killing (e.g., either directly or indirectly causing death of) HNSCC cells in a vertebrate, such as a human cancer patient.

The anti-NKG2A agent (e.g., an anti-NKG2A antibody) can be administered as monotherapy or in adjunctive or combined administration (co-administration) with a second therapeutic agent. The adjunctive or combined administration includes simultaneous administration of the compounds in the same or different dosage form, or separate administration of the compounds (e.g., sequential administration). Thus, the anti-NKG2A and second therapeutic agent can be simultaneously administered in a single formulation.

Alternatively, the anti-NKG2A and second therapeutic agent can be formulated for separate administration and are administered concurrently or sequentially. The second therapeutic agent will normally be administered in amounts and treatment regimens typically used for that agent in a monotherapy for the particular disease or condition being treated. In one embodiment, the second therapeutic agent is an antibody that is capable of mediating ADCC (e.g. binds, via its Fc domain to one or more human Fcγ receptors, e.g., CD16). In one embodiment, the antibody comprises one or more antigen binding domains (e.g. VH-VL pairs) that bind to a polypeptide expressed by a tumor cell, and an Fc domain that binds, via its Fc domain to one or more human Fcγ receptors, e.g., CD16. In one embodiment, the antibody that mediates ADCC is administered in an effective amount that elicits antibody-dependent cellular cytotoxicity toward human tumor cells in the human patient (in vivo) that express a polypeptide to which the second anti-cancer agent is directed.

In one example, the second therapeutic agent is an agent that binds and/or inhibits epidermal growth factor receptor (EGFR).

In one embodiment, the anti-EGFR antibody used is an antibody as described in WO2006/082515, WO2008/017963, WO2002/100348, WO2004/056847, WO2005/056606, WO2005/012479, WO2005/10151, U.S. Pat. No. 6,794,494, EP1454917, WO2003/14159, WO2002/092771, WO2003/12072, WO2002/066058, WO2001/88138, WO98/50433, WO98/36074, WO96/40210, WO 96/27010, US2002065398, WO95/20045, EP586002, U.S. Pat. No. 5,459,061 or 4,943,533. The agent that binds and/or inhibits may thus be an anti-EGFR antibody, e.g., a chimeric antibody, a human antibody or a humanized antibody. An anti-EGFR antibody used in the method of the present disclosure may have any suitable affinity and/or avidity for one or more epitopes contained in EGFR. Preferably, the antibody used binds to human EGFR with an equilibrium dissociation constant ($K_D$) of at most $10^{-8}$ M, preferably at most $10^{-10}$ M. In one embodiment, an anti-EGFR antibody comprises an Fc domain that retains Fcγ (e.g. CD16) binding. In one embodiment, an anti-EGFR antibody comprises a Fc domain of human IgG1 or IgG3 isotype.

The c225 antibody (cetuximab, ERBITUX®) is an example of an anti-EGFR antibody; cetuximab was demonstrated to inhibit EGF-mediated tumor cell growth in vitro and to inhibit human colorectal tumors in vivo received marked approval in 2003. It is a chimeric human/mouse monoclonal antibody that targets the epidermal growth factor receptor (EGFR). Other anti-EGFR antibodies are known that share some or all of all the biological activities of cetuximab such as preventing ligand binding of the EGFR, preventing activation of the EGFR receptor and the blocking of the downstream signalling of the EGFR pathway resulting in disrupted cell growth. Other examples of antibodies for use in the present disclosure include zalutumumab (2F8, described in WO02/100348 and WO04/056847), nimotuzumab (h-R3), panitumumab (ABX-EGF), and matuzumab (EMD72000), antibodies having the CDRs of the rat ICR62 antibody (WO2010/112413), necitumumab (IMC-11F8, Eli Lilly) or a variant antibody of any of these, or an antibody which is able to compete with any of these, such as an antibody recognizing the same epitope as any of these. Competition may be determined by any suitable technique. In one embodiment, competition is determined by an ELISA. Often competition is marked by a significantly greater relative inhibition than 5%, 10% or 25%, as determined by ELISA analysis.

An anti-EGFR antibody or other antibody that mediates ADCC can also be made advantageously with modifications that increase their ability to bind Fc receptors, which can for example affect effector functions such as antibody-dependent cytotoxicity, mast cell degranulation, and phagocytosis, as well as immunomodulatory signals such as regulation of lymphocyte proliferation and antibody secretion. Typical modifications include modified human constant regions comprising at least one amino acid modification (e.g. substitution, deletions, insertions), and/or altered types of glycosylation, e.g., hypofucosylation. Such modifications can affect interaction with Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors while FcγRIIB (CD32B) is an inhibiting (i.e., immune system dampening) receptor. A modification may, for example, increase binding of the Fc domain to an activating Fcγ, e.g. FcγRIIIa, on effector (e.g. NK) cells, or may decrease binding of the Fc domain to an inhibiting Fcγ, e.g. FcγRIIB. Any combination of Fc modifications can be made, for example any combination of different modifications disclosed in U.S. Pat. Nos. 7,632,497; 7,521,542; 7,425,619; 7,416,727; 7,371,826; 7,355,008; 7,335,742; 7,332,581; 7,183,387; 7,122,637; 6,821,505 and 6,737,056; in PCT Publication Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249 and WO 04/063351; and in Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604).

Anti-EGFR antibodies or other antibodies that mediate ADCC may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 333, 334, 335, 337, 338, 339, 340, 359, 360, 370, 373, 376, 378, 392, 396, 399, 402, 404, 416, 419, 421, 430, 434, 435, 437, 438 and/or 439. In one embodiment, a variant Fc region comprises a substitution at any one or more of positions 329, 298, 330, 332, 333 and/or 334 (e.g. S239D, S298A, A330L, I332E, E333A and/or K334A substitutions). Anti-EGFR antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 329, 298, 330, 332, 333 and/or 334 (e.g. S239D, S298A, A330L, I332E, E333A and/or K334A substitutions).

In one embodiment, antibodies having variant or wild-type Fc regions may have altered glycosylation patterns that increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No. 1,176,195; and PCT Publications WO 06/133148, WO 03/035835, and WO 99/54342, each of which is incorporated herein by reference in its entirety. Generally, such antibodies with altered glycosylation are "glyco-optimized" such that the antibody has a particular N-glycan structure that produces certain desirable properties, including but not limited to, enhanced ADCC and effector cell receptor binding activity when compared to non-modified antibodies or antibodies having a naturally occurring constant region and produced by murine myeloma NS0 and Chinese Hamster Ovary (CHO) cells (Chu and Robinson, Current Opinion Biotechnol. 2001, 12: 180-7), HEK293T-expressed antibodies, or other mammalian host cell lines commonly used to produce recombinant therapeutic antibodies.

Monoclonal antibodies produced in mammalian host cells contain an N-linked glycosylation site at Asn297 of each heavy chain. Glycans on antibodies are typically complex biatennary structures with very low or no bisecting N-acetylglucosamine (bisecting GlcNAc) and high levels of core fucosylation. Glycan temini contain very low or no terminal sialic acid and variable amounts of galactose. For a review of effects of glycosylation on antibody function, see, e.g., Wright & Morrison, Trend Biotechnol. 15:26-31(1997). Considerable work shows that changes to the sugar composition of the antibody glycan structure can alter Fc effector functions. The important carbohydrate structures contributing to antibody activity are believed to be the fucose residues attached via alpha-1,6 linkage to the innermost N-acetylglucosamine (GlacNAc) residues of the Fc region N-linked oligosaccharides (Shields et al., 2002).

Historically, antibodies produced in CHO cells contain about 2 to 6% of the population that are nonfucosylated. YB2/0 (rat myeloma) and Lec13 cell line (a lectin mutant of CHO line which has a deficient GDP-mannose 4,6-dehydratase leading to the deficiency of GDP-fucose or GDP sugar intermediates that are the substrate of alpha6-fucosyltransferase have been reported to produce antibodies with 78 to 98% non-fucosylated species. In other examples, RNA interference (RNAi) or knock-out techniques can be employed to engineer cells to either decrease the FUT8 mRNA transcript levels or knock out gene expression entirely, and such antibodies have been reported to contain up to 70% non-fucosylated glycan.

An anti-EGFR antibody or other antibody that mediates ADCC can for example be glycosylated with a sugar chain at Asn297, said antibody showing increased binding affinity via its Fc portion to FcγRIII. In one embodiment of the invention, an antibody will comprise a constant region comprising at least one amino acid alteration in the Fc region that improves antibody binding to FcγRIIIa and/or ADCC.

As used herein, adjunctive or combined administration (co-administration) includes simultaneous administration of the compounds in the same or different dosage form, or separate administration of the compounds (e.g., sequential administration). Thus, the anti-NKG2A and the second therapeutic agent can be simultaneously administered in a single formulation. Alternatively, the anti-NKG2A and the second therapeutic agent can be formulated for separate administration and are administered concurrently or sequentially.

In the treatment methods, the anti-NKG2A antibody and the second therapeutic agent can be administered separately, together or sequentially, or in a cocktail. In some embodiments, the antigen-binding compound is administered prior to the administration of the second therapeutic agent. For example, the anti-NKG2A antibody can be administered approximately 0 to 30 days prior to the administration of the second therapeutic agent. In some embodiments, an anti-NKG2A antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, an anti-NKG2A antibody is administered concurrently with the administration of the second therapeutic agent. In some embodiments, an anti-NKG2A antibody is administered after the administration of the second therapeutic agent. For example, an anti-NKG2A antibody can be administered approximately 0 to 30 days after the administration of the second therapeutic agent. In some embodiments, an anti-NKG2A antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

Suitable treatment protocols for treating a human having cancer include, for example, administering to the patient an effective amount of each of an antibody that inhibits NKG2A and an antibody that binds and/or inhibits human EGFR, wherein the method comprises at least one administration cycle in which at least one dose of the anti-NKG2A antibody is administered at a dose of 1-10 mg/kg body weight and at least one dose of the anti-EGFR antibody is administered at a dose of 1-20 mg/kg body weight. In one embodiment, the administration cycle is between 2 weeks and 8 weeks.

In one embodiment, when administered in combination with an anti-EGFR antibody, an anti-NKG2A is administered in an amount effective to neutralize NKG2A receptors on lymphocytes for at least one week, two weeks, three weeks or four weeks. Anti-NKG2A antibody having an affinity (KD value) for single chain NKG2A-CD94-mFc polypeptides in the picomolar range, notably the antibody having the heavy and light chains of SEQ ID NOS: 2 and 7, respectively having an affinity (KD value) for single chain NKG2A-CD94-mFc polypeptides of 67 pM, at a dose of 1-10 mg/kg results in neutralization of NKG2A on peripheral blood lymphocytes when administered every two weeks.

In one embodiment, the method comprises at least one administration cycle, wherein the cycle is a period of eight weeks or less, wherein for each of the at least one cycles, two, three or four doses of the anti-NKG2A antibody are administered at a dose of 1-10 mg/kg body weight and two, three or four doses of the anti-EGFR antibody are administered at a dose of 0.1-20 mg/kg body weight.

In certain embodiments, a dose (e.g. each dose) of the anti-NKG2A antibody is administered at 10 mg/kg. In certain embodiments, a dose (e.g. each dose) of the anti-EGFR antibody is administered at 1-20 mg/kg, optionally at 1-10 mg/kg, optionally at 1-5 mg/kg (e.g. about 1, 2, 3, 4 or 5 mg/kg).

In one embodiment, cetuximab is administered as a 400 mg/m2 initial dose, followed by 250 mg/m2 weekly, optionally once every 2 weeks. In one embodiment, panitumumab (Vectibix, Amgen) is administered at a dose of 6 mg/kg every 2 weeks.

In certain embodiments, the combined therapy permits the anti-EGFR antibody to be administered at a lower dose than the maximal or the approved dose (e.g., as sole agent, or in the absence of anti-NKG2A).

In one embodiment, the anti-NKG2A antibody and anti-EGFR antibody are administered at the following doses:
(a) 10 mg/kg of anti-NKG2A antibody and 1-10 mg/kg (e.g., 250 mg/m$^2$) of anti-EGFR antibody;
(b) less than 10 mg/kg of anti-NKG2A antibody (e.g., at least 1 mg/kg) and 1-10 mg/kg (e.g., 250 mg/m$^2$) of anti-EGFR antibody.

In one aspect of any of the embodiments herein, the anti-NKG2A antibody is administered once about every two or four weeks. In one aspect of any of the embodiments herein, the anti-EGFR antibody is administered once about every week. In one aspect of any of the embodiments herein, the anti-EGFR antibody is administered once about every two weeks. In one aspect of any of the embodiments herein, the anti-EGFR antibody is administered once about every four weeks.

In one example, a method comprises at least one administration cycle in which one dose of the anti-NKG2A antibody is administered at a dose of 1-10 mg/kg body weight and at least one dose of the anti-EGFR antibody is administered at a dose of 1-10 mg/kg body weight, where the anti-NKG2A antibody is administered once about every two weeks, optionally once every four weeks, and the anti-EGFR antibody is administered once about every week or once every two weeks. In one embodiment, the administration cycle is between 2 weeks and 8 weeks. In one embodiment, the administration cycle is 2 weeks.

In one example, the anti-EGFR antibody is cetuximab, and is administered once every two weeks. For example, a treatment comprises at least one administration cycle in which one dose of the anti-NKG2A antibody is administered at a dose of 1-10 mg/kg body weight and at least one dose of the anti-EGFR antibody is administered at a dose of 1-10 mg/kg body weight (optionally with a higher dose of anti-EGFR for the first administration of anti-EGFR), where the anti-NKG2A antibody is administered once about every two weeks and the anti-EGFR antibody is administered once about every two weeks.

In one embodiment, provided is a method for assessing whether an individual is suitable for treatment with an agent that inhibits NKG2A and an agent that binds (and, e.g., induces ADCC towards) and/or inhibits the activity of human EGFR, the method comprising detecting a tumor cell (e.g. a HNSCC tumor cell) that expresses both an HLA-E nucleic acid or polypeptide and an EGFR nucleic acid or polypeptide in a biological sample from an individual. A determination that the individual has a tumor cell (or tumor cell population) that expresses both HLA-E nucleic acid or polypeptide and EGFR nucleic acid or polypeptide indicates that the patient has a cancer that can be treated with an agent that inhibits NKG2A in combination with an agent that binds and/or inhibits the activity of human EGFR.

EXAMPLES

Example 1—Effect of a Dose-Response of Anti-NKG2A on NK Cell Activation

Immunotherapeutic approaches for HNSCC are particularly complicated by the profound immune suppression that is induced by HNSCC, which potentially decreases the effectiveness of immune stimulatory efforts (see, e.g., Duray et al. (2010) Clin. Dev. Immunol. 2010: 1-15). The goal of this experiment was to explore whether an anti-NKG2A antibody that targets NKG2A is able to eliminate HNSCC cells.

Effect of a dose-response of anti-NKG2A on NK cell activation was determined by analysis of CD107 and CD137 expression. CD107 mobilization in 4 hours is a marker of the release of lytic granules by NK cells (Alter et al., (2004) J Immunol Methods 294(1-2): 15-22). Increase in CD137 expression in 24 hours is correlated with the activation of several lymphocytes including NK cells (Kohrt et al. (2011) Blood 117(8):2423-2432). Analysis of CD107 and CD137 expression was performed on NK cells expressing or not expressing NKG2A (NKG2A+NK cells or NKG2A-NK cells respectively). As the antibody is targeting NKG2A, its effect is expected to be seen only on NKG2A+NK cells, and thus NKG2A-NK cells can be regarded as an internal control in the experiments.

The effector cells used were freshly isolated PBMC from healthy volunteers and target cells were HNSCC cell lines or clones of K562 cell line transfected with HLA-E. Cells were numerated and passed every two days in complete medium. They were kept in culture up to 12 passages. The day before of the experiment, cells were counted and adjusted to 100,000 cells/well. Viability was measured and had to be over 90%.

The K562 cell lines were K562 clone E6 (HLA-E positive, CD32low) and K562 clone F7 (HLA-E negative/low, CD32low). Human head and neck cancer cell lines were screened by flow cytometry for HLA-E expression (see Table C, below). Three cell lines were selected for functional tests: FaDu (ATCC #HTB-43), H-N(DSMZ #ACC 417) and CAL-27 (DSMZ #ACC 446).

4 hours vs. CD137 at 24 hours. 7 donors (FaDu and H-N) and 2 donors (CAL-27) were tested. Anti-NKG2A antibody whose heavy chain amino acid sequence is shown in SEQ ID NO: 2 and whose light chain amino acid sequence is shown in SEQ ID NO: 7 was used at a final concentration of 10 µg/mL.

Figure 1B:
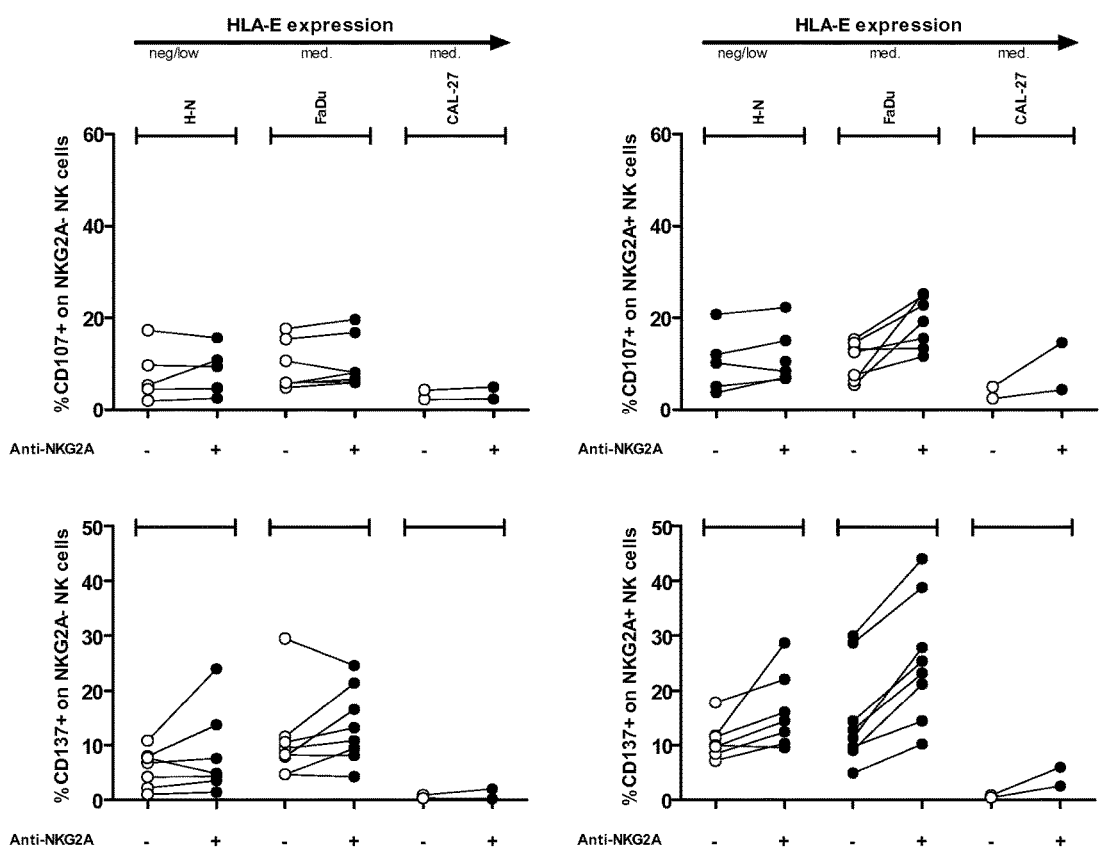

FIGS. 1A and 1B show CD107 (Top) and CD137 (Bottom) FACS read-outs on NKG2A-NK (left) or NKG2A+NK cells (right) in presence of controls or indicated target cell lines and in presence or not of anti-NKG2A at a saturating dose of 10 µg/mL. The cell lines are ordered from left to right according to level of HLA-E surface expression. Each dot represents PBMC from a healthy volunteer. FIG. 1B shows HNSCC cell lines and demonstrates anti-NKG2A can restore lysis of HNSCC with endogenous HLA-E expression or of K562 transfected with HLA-E. This effect is only seen on NKG2A positive NK cells and is dependent on the level of expression of HLA-E. Indeed, anti-NKG2A effect is seen on cell lines with medium to high levels of HLA-E expression.

Anti-NKG2A can induce the NK-mediated lysis of HLA-E expressing cell lines by blocking the interaction of the inhibitory receptor NKG2A with HLA-E. This effect is observed on K562 cell line transfected with HLA-E, but more importantly on HNSCC cell lines with endogenous HLA-E expression such as FaDu and CAL-27 cell lines. The extent of anti-NKG2A effect depends on the level of HLA-E expression at the cell surface of the target cells.

Example 2—HLA-E Suppression of Anti-EGFR Activity can be Overcome by Anti-NKG2A Epidermal growth factor receptor (EGFR) (also ErbB-1; HER1 in humans) is a ubiquitously expressed transmembrane glycoprotein in the ErbB/HER family of receptor tyrosine kinase. High expression of EGFR occurs in most epithelial malignancies including HNSCC and is associated with a poor prognosis. Its activation through natural ligands leads to the initiation of intracellular signaling pathways that regulate the activation of cell proliferation, invasion, angiogenesis and metastasis driving tumor growth.

TABLE C

| | HLA-E expression | | | |
|---|---|---|---|---|
| Cell line | Mean HLA-E/ IC MFI ratio | # exp. | Cell type | Source |
| H-N | 2.8 | n = 2 | Oral squamous cell carcinoma | DSMZ, Germany |
| Detroit 562 | 2.7 | n = 1 | Pharynx carcinoma (metastatic site: pleural effusion) | ATCC, USA |
| SCC-9 | 3.7 | n = 1 | Tongue squamous carcinoma | ATCC, USA |
| A-253 | 3.5 | n = 1 | Submaxillary salivary gland; epidermoid carcinoma | ATCC, USA |
| FaDu | 5.2 | n = 2 | Pharynx squamous cell carcinoma | ATCC, USA |
| BICR6 | 1.8 | n = 1 | Hypopharynx squamous cell carcinoma | Public Health England, UK |
| BICR16 | 2.4 | n = 1 | Tongue squamous carcinoma | Public Health England, UK |
| CAL-27 | 4.0 | n = 2 | Tongue squamous carcinoma | DSMZ, Germany |
| BICR10 | 2.3 | n = 1 | Buccal mucosa squamous carcinoma | Public Health England, UK |

The effector cells used were freshly isolated PBMC from healthy volunteers. Target cells were the HNSCC cell lines FaDu, H—N and CAL-27, and clones of K562 cell line transfected with HLA-E (Clone E6=HLA-E+, clone F7=HLA-E) as an E:T ratio 2.5/1. Read out was CD107 at The anti-EGFR monoclonal antibody cetuximab is thought to act through blocking oncogenic signaling of the EGF receptor pathway and by inducing Fcγ receptor-mediated antibody dependent cellular cytotoxicity (ADCC). In HNSCC however, ADCC may be affected by the profound immune suppression that is induced. At the same time, blocking oncogenic signaling of the EGF receptor pathway results in posttranscriptional regulation in tumor cells of major histocompatibility complex (MHC) class I-related antigens of the MICA/B and ULBP protein families which are recognized by the activating receptor NKG2D on NK cells and subsets of T cells. In particular, the expression by tumor cells of these stress-related antigens which are the natural ligands of NKG2D is decreased by clinical EGFR inhibitors, thus potentially decreasing the tumor cells' visibility to NK and T cells (Vantourout et al., Sci. Transl. Med. 6: 231ra49 (2014)

This experiment was designed to explore the effect of an EGFR inhibiting antibody on the ability of anti-NKG2A antibodies to activate NK cells in HNSCC. Effect of a dose-response of cetuximab on NK cell activation was determined by analysis of CD107 and CD137 expression (see Example 1 for an overview of methods), using as effector cells PBMC freshly isolated from healthy volunteers, and as target cells HNSCC cell lines FaDu and H-N at an E:T ratio of 2.5/1. The read out was CD107 at 4 hours vs. CD137 at 24 hours, using 3 donors (CD107 read out in 4h) and four donors (CD137 read out in 24h). Cetuximab was tested at a dose response, 1/10 serial dilution starting at 10 µg/mL. For one healthy volunteer, NK cells were subdivided in NKG2A+ and NKG2A-subsets. Suboptimal doses of cetuximab were chosen for further testing to explore the effect of an EGFR inhibiting antibody on the ability of anti-NKG2A antibodies to activate NK cells in HNSCC. The 0.001 µg/mL (1 ng/mL) dose is the starting point of the cetuximab effect observed both with CD107 and CD137 readouts. The 0.01 µg/mL (10 ng/mL) dose is approximatively at the EC50 of the cetuximab effect.

The combined effect of anti-NKG2A and a sub-optimal dose of EGFR inhibitor was assessed by analysis of CD107 and CD137 expression (see Example 1 for an overview of methods), using as effector cells freshly isolated PBMC from healthy volunteers, and as target cells HNSCC cell lines FaDu, H—N and CAL-27 clones of K562 cell line transfected with HLA-E (Clone E6=HLA-E$^+$, clone F7=HLA-E), at an E:T ratio of 2.5/1. The read out was CD107 at 4 hours vs. CD137 at 24 hours, using 7 donors (FaDu and H-N) and two donors (CAL-27).

Anti-NKG2A antibody whose heavy chain amino acid sequence is shown in SEQ ID NO: 2 and whose light chain amino acid sequence is shown in SEQ ID NO: 7 was used at a final concentration of 10 µg/mL corresponding to a saturating dose, and EGFR inhibitor cetuximab was used at two suboptimal doses of 0.001 µg/mL or 0.01 µg/mL.

Figure 2:
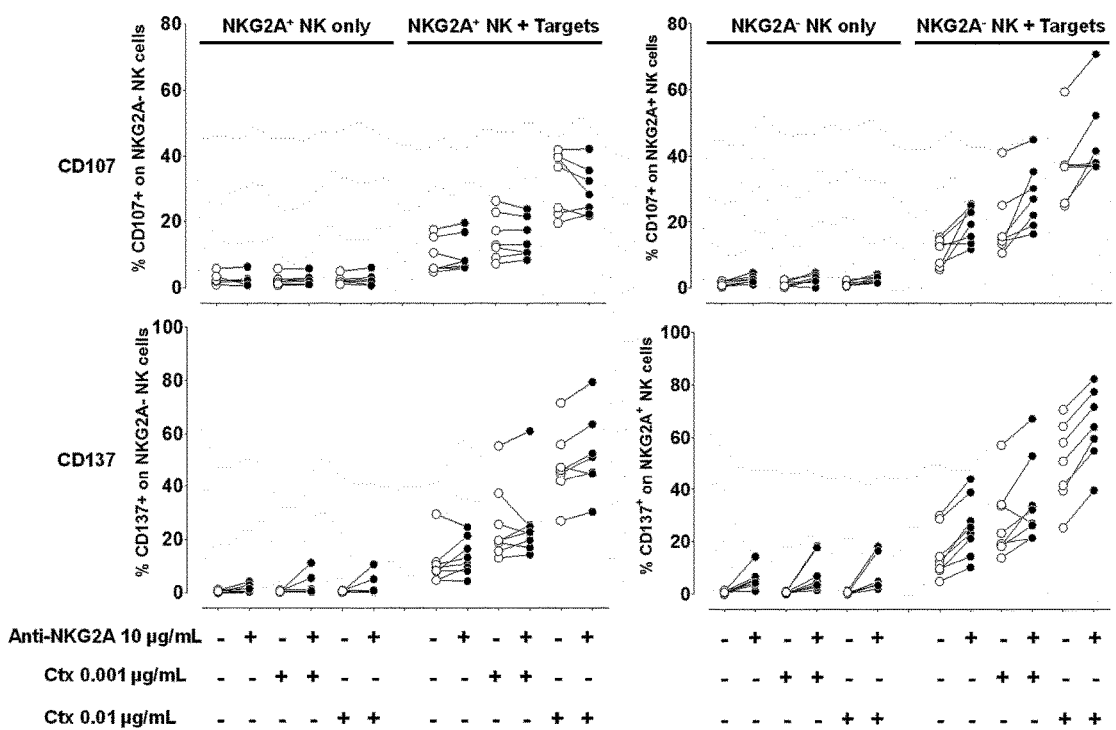
FIG. 2 shows saturating doses of anti-NKG2A enhanced ADCC by NK cells toward HNSCC FaDu cells induced by suboptimal doses of anti-EGFR (cetuximab (ctx)).

Saturating doses of Anti-NKG2A enhanced ADCC to HNSCC cell lines induced by suboptimal doses of cetuximab. No cetuximab-dependent ADCC was observed on K562 transfected cell lines as they do not express EGF-R. Anti-NKG2A effect is only seen on NKG2A positive NK cells, and is dependent on the level of expression of HLA-E. Indeed, anti-NKG2A effect is seen on cell lines with medium to high levels of HLA-E expression (FaDu, CAL-27 and K562-HLA-E clone E6). FIG. 2 is a representative example, shown for FaDu cells. It can be seen in FIG. 2 that saturating doses of anti-NKG2A enhanced ADCC to HNSCC cell lines induced by suboptimal doses of cetuximab (ctx).

Example 3—Combined Effect of Increasing Doses of Anti-NKG2A with Increasing Doses of Cetuximab The effect of the combination of increasing doses of EGFR inhibiting antibody and increasing doses of anti-NKG2A antibodies was evaluated for the ability to activate NK cells toward HNSCC target cells. Experiments sought to evaluate whether anti-NKG2A therapy can still enhance ADCC when cetuximab is used at a saturating dose, and whether the anti-NKG2A effect is dose-dependent.

Briefly, effector cells used were freshly isolated PBMC from healthy volunteers, and target cells were HNSCC cell lines FaDu, H—N and CAL-27, and clones of K562 cell line transfected with HLA-E (Clone E6=HLA-E$^+$, clone F7=HLA-E), and an E:T ratio of 2.5/1. The read out was CD107 at 4 hours vs. CD137 at 24 hours, using 2 donors. Anti-NKG2A antibody whose heavy chain amino acid sequence is shown in SEQ ID NO: 2 and whose light chain amino acid sequence is shown in SEQ ID NO: 7 was used at two suboptimal doses of 0.1 and 1 µg/mL, and at a saturating dose of 10 µg/mL. Cetuximab was used at two suboptimal doses of 0.001 µg/mL and 0.01 µg/mL (~EC50) and at a saturating dose of 0.1 µg/mL in these experimental settings.

Figure 3A:
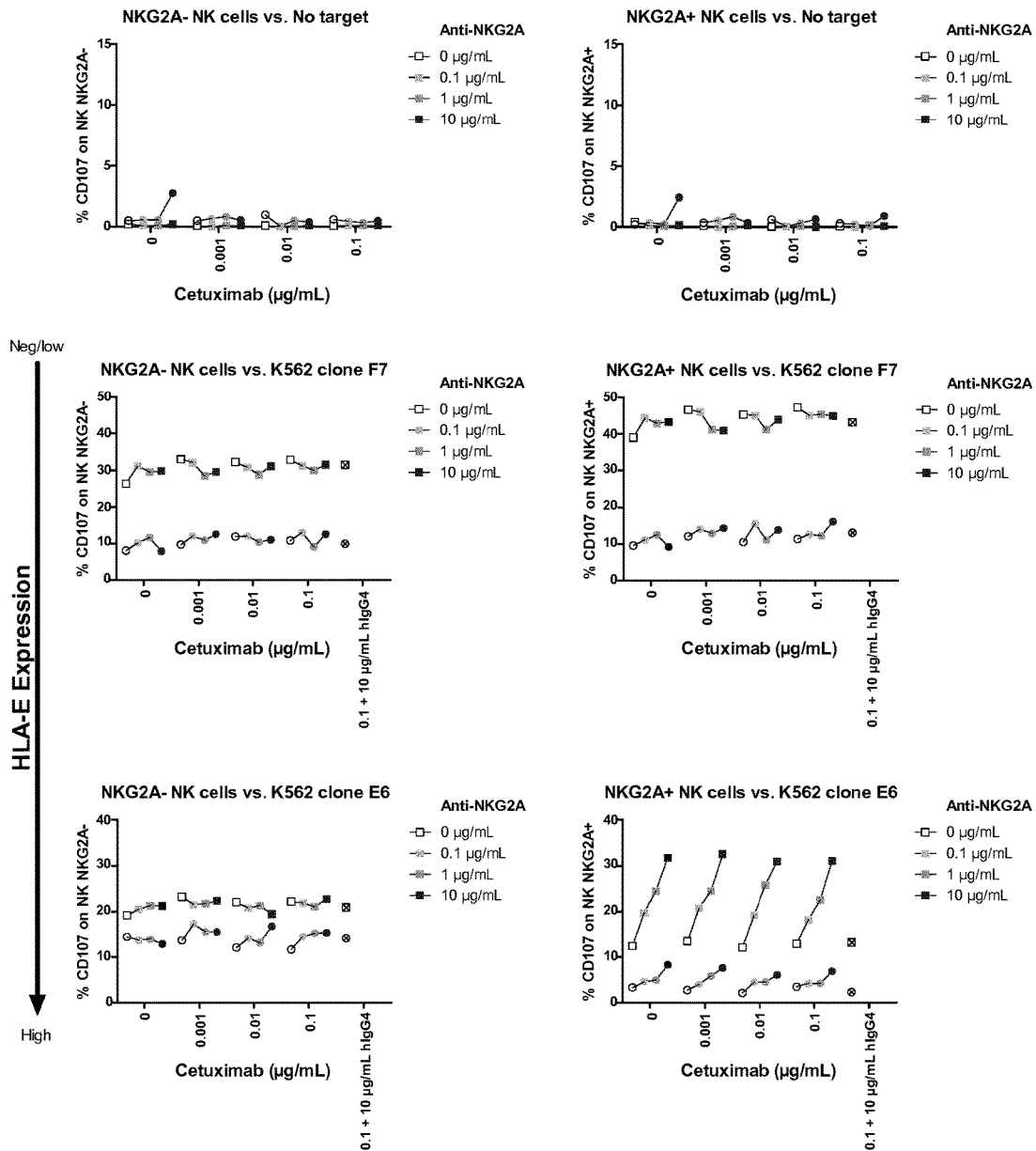
FIGS. 3A and 3B show effect of increasing doses of anti-NKG2A and increasing doses of anti-EGFR (cetuximab).
Figure 3B:
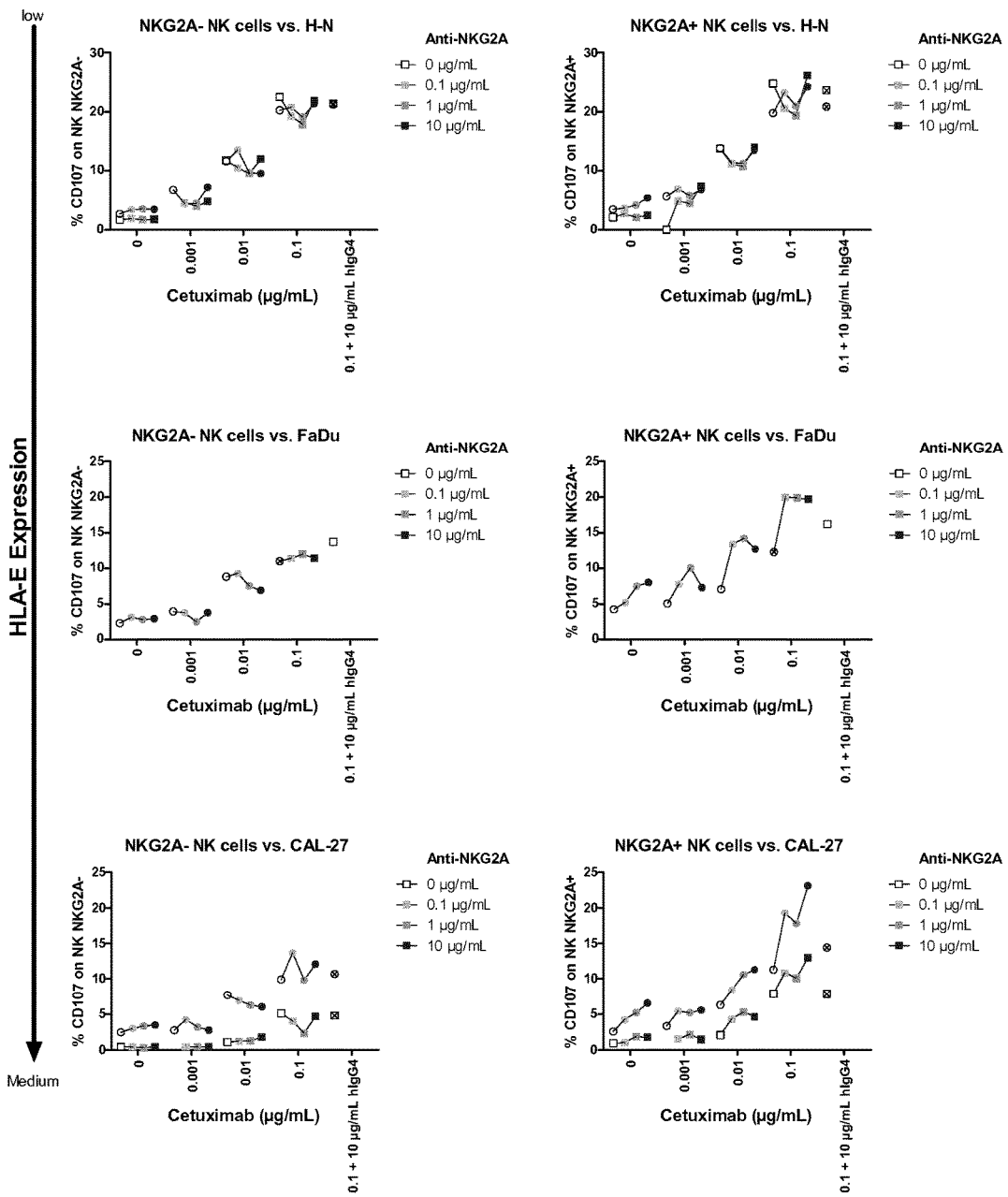

Results are shown in FIGS. 3A and 3B. FIG. 3A shows CD107 read out on controls with no target and with K562-HLA-E transfectants. Each healthy volunteer is represented by a different symbol: squares or circles. Crossed open symbols correspond to condition where anti-NKG2A was replaced by 10 µg/mL hIgG4 isotypic control co-incubated with 0.1 µg/mL cetuximab. It can be seen that the effect of anti-NKG2A antibody is dose-dependent, depends on HLA-E expression level, and is still observed at a saturating dose of cetuximab of 0.1 µg/mL in clone E6 that expresses HLA-E at high levels. In clone F7 (low HLA-E expression levels), the effect of anti-NKG2A was limited and high doses (e.g. saturating doses) of anti-NKG2A did not further augment the effect.

FIG. 3B shows CD107 read out on HNSCC cell lines. Each healthy volunteer is represented by a different symbol: squares or circles. Crossed open symbols correspond to condition where anti-NKG2A was replaced by 10 µg/mL hIgG4 isotypic control co-incubated with 0.1 µg/mL cetuximab. It can be seen that the effect of anti-NKG2A antibody is dose-dependent, depends on HLA-E expression level, and is still observed at a saturating dose of cetuximab of 0.1 µg/mL in the FaDu or CAL-27 that expresses at higher levels/stain strongly for HLA-E.

The effect of anti-NKG2A antibody is dose-dependent, depends on HLA-E expression level, and is still observed at a saturating dose of cetuximab of 0.1 µg/mL.

Example 4—HLA-E is Consistently Expressed in HNSCC Including in HPV16 Genotypes

Expression of HLA-E on tumors of HNSCC patients was studied. Samples were obtained from 20 patients having disease of clinical stage III, IV or IVA cancer squamous cell carcinoma, NOS (16 primary tumors & 4 metastatic tumors (LN)) with tumor grades I to IV. The breakdown was: oral cavity and/or floor (n=3), larynx (n=6), pharynx (n=1), tongue, (n=7), tonsil (n=3). HPV16 genotype (14/20 positive) and HPV P16$^{Inka}$ detection (7/14 positive).

Staining was performed on frozen tissue sections using murine IgG1 anti-human HLA-E (3D12) at 5 µg/ml to stain HLA-E and mouse IgG1 anti-NKG2A (Z270) at 5 µg/ml to stain NKG2A, compared with isotype control: murine IgG1 (DAKO A/S, Denmark) at 5 µg/ml. Detection was carried out using the EnVision™ detection kit (DAKO A/S, Denmark). Healthy human positive control tissues were included (placenta, tonsil and lymph node), as well as transfected cell lines. Separately, tumor and stromal lymphocyte infiltration was assessed in the tumor samples.

The HLA-E and NKG2A staining protocol used was as follows: bring to room temperature, rehydrate with PBS, block endogenous peroxydase 0.3% $H_2O_2$ in PBS, wash PBS 3X, saturate with PBS Goat serum 5%, incubate with Ab diluted in PBS 100p1, wash PBS 3X, incubate with envision kit (2 drops), wash PBS 3X, incubate with DAB 100p1, rinse $H_2Od$, Incubate with hematoxylin (2 drops), rinse $H_2Od$, OTTIX shaper bath, OTTIX plus bath, and mount with Diamount slide cutter and mounter.

In addition to scoring for level of staining 0-3, the cell type and cellular localization of the signal was recorded when present. It was classified as membranous, cytoplasmic or extracellular for the cellular localization.

IHC scoring was performed as follows:
0: negative signal
1: faint to weak signal in <25-50% of the cell type
2: intermediate signal in intensity but expressed in >50% of the cell type or strong signal, but expressed in <25-50% of the cell type
3: strong signal diffusely expressed across all cells within cellular subtype Results showed diffuse cytoplasmic staining for HLA-E ranging from 1+ to 3+. The HLA-E staining was across different tumor locations/types and included HPV positive patients, including HPV16 genotype and samples characterized by HPV $P16^{INK4}$ expression.

Figure 4:
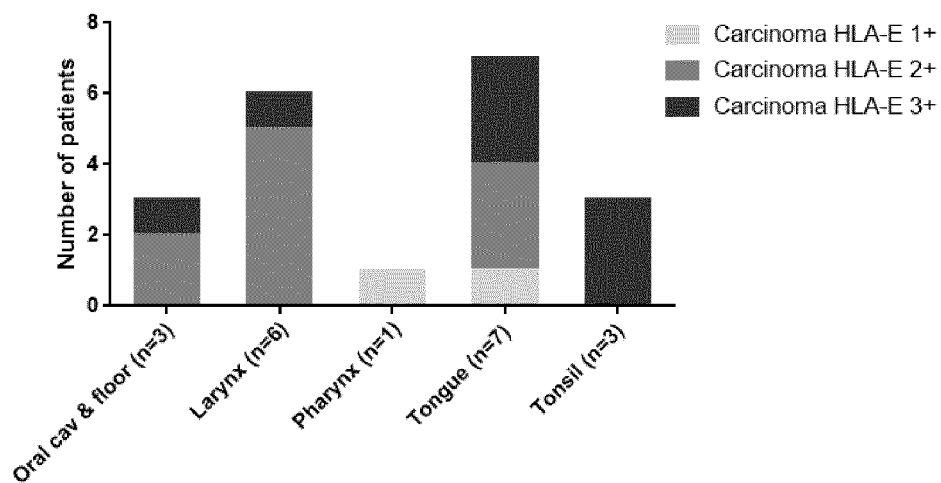
FIG. 4 shows HLA-E staining ranging from 1+ to 3+ in head and neck squamous cell carcinomas of different tumor locations/types. Interestingly, staining was 3+ in all samples from the tumor type generally recognized as having the worst prognosis (tonsil).

FIG. 4 shows HLA-E staining ranging from 1+ to 3+ in different tumor locations/types. Interestingly, staining was 3+ in all samples from the tumor type generally recognized as having the worst prognosis (tonsil).

Figure 5:
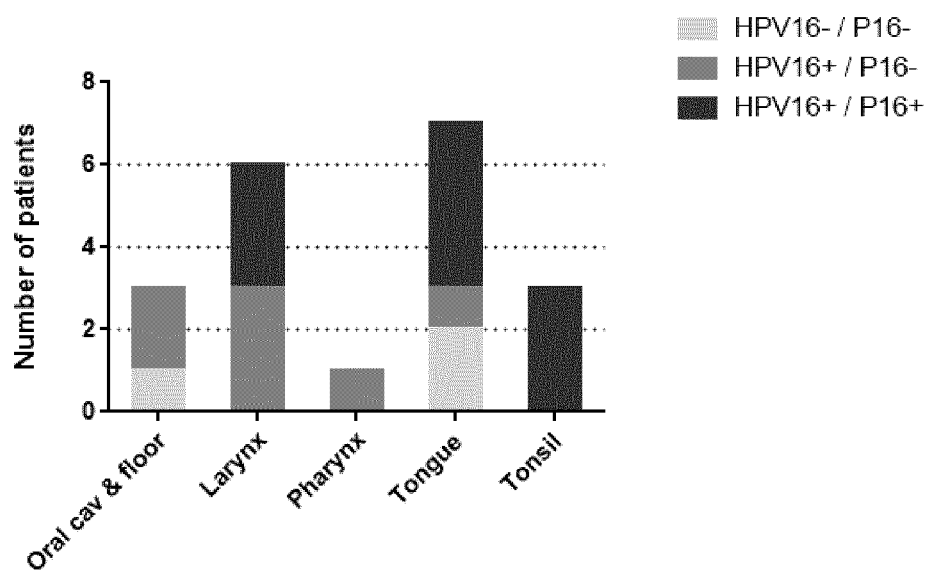
FIG. 5 shows the detail on the HPV16 and P16 status for patients of different tumors.
Figure 6:
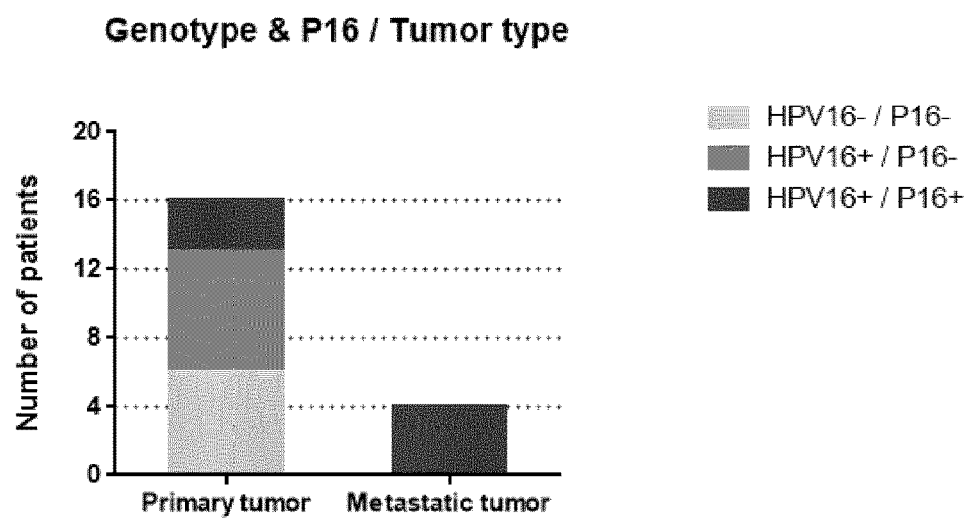
FIG. 6 shows tumor types (metastatic or primary tumor) as a function of HPV16 and P16$^{INK4}$.
Figure 7:
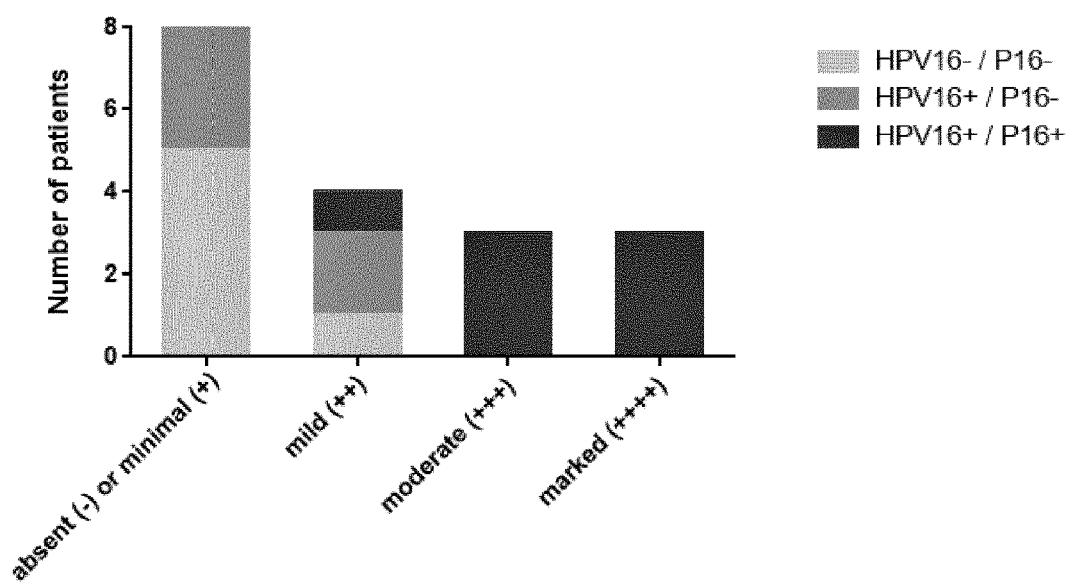
FIG. 7 shows that HPV-positive tumors were characterized by strong lymphocyte infiltration.

Results also showed that HLA-E is consistently expressed in HPV positive patients, including the HPV16 genotype. FIG. 5 shows the detail on the HPV16 and P16 status for patients with different tumors; all samples from the tumor type (tonsil) generally recognized as having the worst prognosis were both HPV16 positive and $P16^{INK4}$ positive. Larynx and tongue tumors were also predominantly HPV16 positive, and with significant share of $P16^{INK4}$ positive samples. FIG. 6 shows tumor type (metastatic or primary tumor) as a function of HPV16 and $P16^{INK4}$; all metastatic tumors were both HPV16 positive, and all were also $p16^{INK4}$ positive. Results further showed that HLA-E expression as well as HPV-positive tumors were characterized by strong lymphocyte infiltration, as shown in FIG. 7. Furthermore, lymphocytes in tumor samples expressed NKG2A, with the strongest staining for NKG2A in patients who were both HPV16 positive and $P16^{INK4}$ positive.

Example 5—A Human Clinical Trial for Treatment of Cancer with Repeated Injections of Humanized Z270 as Single Agent The primary objective of the trial is to evaluate the antitumor activity of pre-operative IPH2201 (humanized anti-NKG2A antibody Z270 comprising a S241P mutation) in patients with operable squamous cell carcinoma of the oral cavity. The secondary objectives are to assess the safety of IPH2201, the pharmacokinetics, the immunogenicity and the pharmacodynamics including intra-tumoral biomarkers.

Trial Design:

The trial is an open label single-arm phase 1b-II study including a run-in part. Previously untreated patients with measurable, clinical intermediate or high risk, stage III or IVa squamous cell carcinoma of the oral cavity will be treated with single agent IPH2201 i.v. every 2 weeks (q2w) for 4 administrations, by intravenous (i.v.) route over 1 hour. The first 6 patients will receive IPH2201 at a dose of 4 mg/kg q2w×4. A minimum interval of one week will be observed between the first administrations of IPH2201 to the 3 first patients treated at 4 mg/kg. The subsequent patients will be treated at a dose of 10 mg/kg q2w×4, the escalation of the dose being allowed by the safety committee after a minimal follow-up of 4 weeks following the first administration in the last patient treated at 4 mg/kg. Standard loco-regional treatment with surgery followed by adjuvant therapy (radiotherapy (RT) or radiochemotherapy (RCT)) according to histopathological risk factors will be initiated after the last administration of IPH2201. In case of tumor progression loco-regional treatment will be initiated immediately.

Antitumor activity is assessed clinically and radiologically before the third administration of IPH2201, and 2 weeks after the last administration of IPH2201, before surgery. Tumor measurements are obtained on target lesions according to RECIST 1.1 criteria. The same imaging techniques are used for efficacy assessment at baseline and during the preoperative period, for the assessment of the primary end point and/or after surgery, for the monitoring of potential relapses. An assessment by appropriate imaging techniques, at the investigator's discretion (computed tomography (CT) scans and/or Magnetic Resonance Imaging (MRI)), is performed in all the patients, as well as photographs of the accessible tumor lesions.

Fresh tumor samples are obtained by biopsy at baseline and the resected specimen are collected at surgery. The patients will be followed up to one year after the first cycle of administration. After the end of study visit, relapse and survival will be documented post study according to local practices for 2 additional years.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention is to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). Where "about" is used in connection with a number, this can be specified as including values corresponding to +1-10% of the specified number.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples or exemplary language (e.g., "such as") provided herein is intended merely to better illuminate the invention and does not pose a limitation on the scope of the invention unless otherwise claimed. No language in the specification should be construed as indicating any non-claimed element as essential to the practice of the invention.

The invention claimed is:

1. A method of treating a head and neck squamous cell carcinoma (HNSCC) in an individual, the method comprising administering to the individual an antibody that binds a human NKG2A polypeptide and neutralizes the inhibitory activity of NKG2A, wherein the NKG2A antibody comprises a heavy chain comprising SEQ ID NO: 2 and a light chain comprising SEQ ID NO: 7.

2. The method of claim 1, wherein the HNSCC is an oral cavity squamous cell carcinoma.

3. The method of claim 1, wherein the HNSCC is an oropharyngeal tumor.

4. The method of claim 1, wherein the HNSCC is a larynx tumor.

5. The method of claim 1, wherein the HNSCC is a tumor of the hypopharynx.

6. The method of claim 1, wherein the individual is human papilloma virus (HPV) positive.

7. The method of claim 1, wherein the treatment of a HNSCC in an individual comprises:
   a) determining whether HLA-E polypeptide is expressed by malignant cells from the individual having a HNSCC; and
   b) upon a determination that malignant cells express HLA-E polypeptide at or above a reference level, administering to the individual an antibody that neutralizes the inhibitory activity of a human NKG2A polypeptide.

8. The method of claim 7, wherein determining whether HLA-E polypeptide is expressed by malignant cells comprises obtaining from the individual a biological sample that comprises HNSCC cells, bringing said cells into contact with an antibody that binds a HLA-E polypeptide, and detecting cells that express HLA-E.

9. The method of claim 1, wherein the antibody comprises an Fc-engineered constant region comprising an amino acid modification that reduces binding to a human Fcγ receptor.

10. The method of claim 1, wherein the anti-NKG2A antibody is administered several times at a dosing frequency from once about every week to once about per month.

11. A method for treatment of a cancer in an individual, wherein the method comprises:
   a) determining the HLA-E polypeptide status of malignant cells from the individual having a cancer;
   b) determining the EGFR polypeptide status of malignant cells from the individual having a cancer; and
   c) upon a determination that HLA-E and EGFR polypeptides are expressed by malignant cells from the individual at levels that are at or above a reference level, administering to the individual a therapeutic regimen that comprises an antibody that neutralizes the inhibitory activity of a human NKG2A polypeptide and cetuximab, wherein the antibody comprises a heavy chain comprising SEQ ID NO: 2 and a light chain comprising SEQ ID NO: 7.

12. A method for treatment of a HNSCC in an individual, wherein the method comprises:
  a) determining whether the individual has a HNSCC characterized by the presence of lymphocytes in the tumor environment; and
  b) upon a determination that the individual has a HNSCC characterized by the presence of lymphocytes in the tumor environment, administering to the individual an antibody that neutralizes the inhibitory activity of a human NKG2A polypeptide, wherein the antibody comprises a heavy chain comprising SEQ ID NO: 2 and a light chain comprising SEQ ID NO: 7.

13. A method of treating a HNSCC in a human patient, the method comprising administering to the patient an effective amount of each of: (a) an antibody that neutralizes the inhibitory activity of human NKG2A, and (b) cetuximab, wherein the antibody that neutralizes the inhibitory activity of human NKG2A comprises a heavy chain comprising SEQ ID NO: 2 and a light chain comprising SEQ ID NO: 7.

14. The method of claim 13, wherein the method comprises at least one administration cycle, wherein the cycle is a period of two weeks, wherein for each of the at least one cycle, one dose of the antibody that neutralizes the inhibitory activity of human NKG2A is administered and two doses of cetuximab are administered.

15. The method of claim 13, wherein the method comprises at least one administration cycle, wherein the cycle is a period of two weeks, wherein for each of the at least one cycle, one dose of the antibody that neutralizes the inhibitory activity of human NKG2A is administered at a dose of 1-10 mg/kg and two doses of cetuximab are administered at a dose of 1-10 mg/kg.

\* \* \* \* \*

UNITED STATES PATENT AND TRADEMARK OFFICE
CERTIFICATE OF CORRECTION

| | | |
|---|---|---|
| PATENT NO. | : 10,329,348 B2 | Page 1 of 1 |
| APPLICATION NO. | : 15/521401 | |
| DATED | : June 25, 2019 | |
| INVENTOR(S) | : Pascale Andre et al. | |

It is certified that error appears in the above-identified patent and that said Letters Patent is hereby corrected as shown below:

In the Specification

Column 1,
Line 62, "(Coupe) et al.," should read --(Coupel et al.,--.

Column 24,
Line 34, "P13 Kinase (P13K)," should read --PI3 Kinase (PI3K),--.

Column 27,
Line 57, "1332E" should read --I332E--.

Signed and Sealed this
Twenty-fifth Day of February, 2020

Andrei Iancu
*Director of the United States Patent and Trademark Office*